(12) United States Patent
Mack

(10) Patent No.: US 10,488,188 B2
(45) Date of Patent: *Nov. 26, 2019

(54) SYSTEM AND METHOD FOR REMOVING NOISE FROM ROUGHNESS MEASUREMENTS

(71) Applicant: FRACTILIA, LLC, Austin, TX (US)

(72) Inventor: Chris Mack, Austin, TX (US)

(73) Assignee: Fractilia, LLC, Austin, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/218,338

(22) Filed: Dec. 12, 2018

(65) Prior Publication Data

US 2019/0113338 A1   Apr. 18, 2019

Related U.S. Application Data

(63) Continuation-in-part of application No. 15/892,080, filed on Feb. 8, 2018, now Pat. No. 10,176,966.

(Continued)

(51) Int. Cl.
| | |
|---|---|
| G01B 15/08 | (2006.01) |
| H01J 37/28 | (2006.01) |
| G03F 7/20 | (2006.01) |

(52) U.S. Cl.
CPC ............ G01B 15/08 (2013.01); G03F 7/705 (2013.01); G03F 7/70625 (2013.01); H01J 37/28 (2013.01); *H01J 2237/2814* (2013.01)

(58) Field of Classification Search
CPC ..... G01B 15/08; G03F 7/705; G03F 7/70616; G03F 7/70625; H01J 37/28; H01J 2237/2814

(Continued)

(56) References Cited

U.S. PATENT DOCUMENTS

| | | |
|---|---|---|
| 7,049,589 B2 | 5/2006 | Yamaguchi et al. |
| 7,310,155 B1 | 12/2007 | Capodieci et al. |

(Continued)

FOREIGN PATENT DOCUMENTS

WO    2018160502 A1    9/2018

OTHER PUBLICATIONS

Mack, et al.—"Modeling Metrology for Calibration of OPC Models", Metrology, Inspection, and Process Control for Microlithograhy XXX, Proc. SPIE vol. 9778 (2016), pp. 1-9.

(Continued)

*Primary Examiner* — Nicole M Ippolito
*Assistant Examiner* — Hanway Chang
(74) *Attorney, Agent, or Firm* — Dickinson Wright PLLC

(57) ABSTRACT

Systems and methods are disclosed that remove noise from roughness measurements to determine roughness of a feature in a pattern structure. In one embodiment, a method for determining roughness of a feature in a pattern structure includes generating, using an imaging device, a set of one or more images, each including measured linescan information that includes noise. The method also includes detecting edges of the features within the pattern structure of each image without filtering the images, generating a biased power spectral density (PSD) dataset representing feature geometry information corresponding to the edge detection measurements, evaluating a high-frequency portion of the biased PSD dataset to determine a noise model for predicting noise over all frequencies of the biased PSD dataset, and subtracting the noise predicted by the determined noise model from a biased roughness measure to obtain an unbiased roughness measure.

28 Claims, 24 Drawing Sheets

Related U.S. Application Data

(60) Provisional application No. 62/678,866, filed on May 31, 2018, provisional application No. 62/739,721, filed on Oct. 1, 2018, provisional application No. 62/602,152, filed on Apr. 13, 2017.

(58) Field of Classification Search
USPC ............ 250/306, 307, 309, 310, 311, 492.1, 250/492.2
See application file for complete search history.

(56) References Cited

U.S. PATENT DOCUMENTS

| | | | |
|---|---|---|---|
| 7,366,620 B2 | 4/2008 | Yamaguchi et al. | |
| 7,633,061 B2 | 12/2009 | Tanaka et al. | |
| 8,013,301 B2 | 9/2011 | Tam | |
| 8,050,898 B2 | 11/2011 | Hansen | |
| 8,108,805 B2 | 1/2012 | Rathsack | |
| 8,142,965 B2 | 3/2012 | Yoel | |
| 8,300,919 B2 | 10/2012 | Yamaguchi et al. | |
| 8,340,393 B2 | 12/2012 | Tam et al. | |
| 8,401,273 B2 | 3/2013 | Momonoi et al. | |
| 8,488,128 B2 | 7/2013 | Brill | |
| 9,236,219 B2 | 1/2016 | Chen et al. | |
| 9,824,938 B2 | 11/2017 | Yamaguchi et al. | |
| 10,176,966 B1* | 1/2019 | Mack | H01J 37/222 |
| 2018/0173839 A1 | 6/2018 | Fang et al. | |
| 2019/0139736 A1* | 5/2019 | Mack | G01N 23/225 |
| 2019/0164303 A1* | 5/2019 | Mack | H01J 37/28 |
| 2019/0180976 A1* | 6/2019 | Mack | H01J 37/28 |
| 2019/0180977 A1* | 6/2019 | Mack | H01J 37/28 |
| 2019/0186909 A1* | 6/2019 | Mack | G01B 11/30 |
| 2019/0187570 A1* | 6/2019 | Mack | G03F 7/70625 |

OTHER PUBLICATIONS

Mack, et al.—"Using the Analytical Linescan Model for SEM Metrology", Metrology, Inspection, and Process Control for Microlithograhy XXXI, Proc. (2017), pp. 1-8.

Mack—"Reducing Roughness in Extreme Ultraviolet Lithography", International Conference on Extreme Ultraviolet Lithography, SPIE vol. 10450, (2017), pp. 1-14.

Lorusso, et al. "Unbiased Roughness Measurements: Subtracting Out SEM Effects", Microelectronic Engineering 190, available Jan. 6, 2018, pp. 33-37.

* cited by examiner

POWER SPECTRAL DENSITY (PSD) VS. FREQUENCY FOR SAMPLE WITH ROUGH EDGE

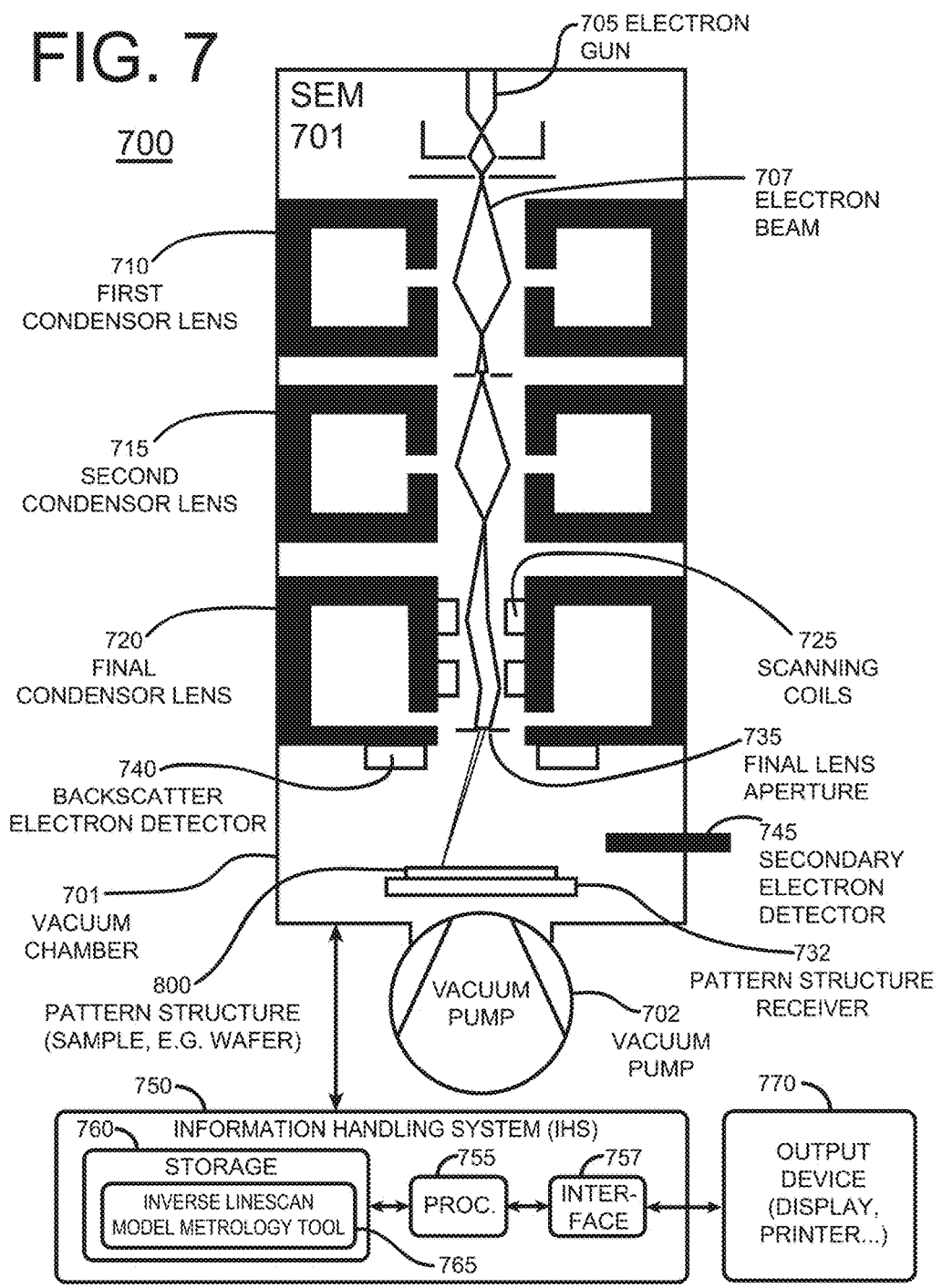

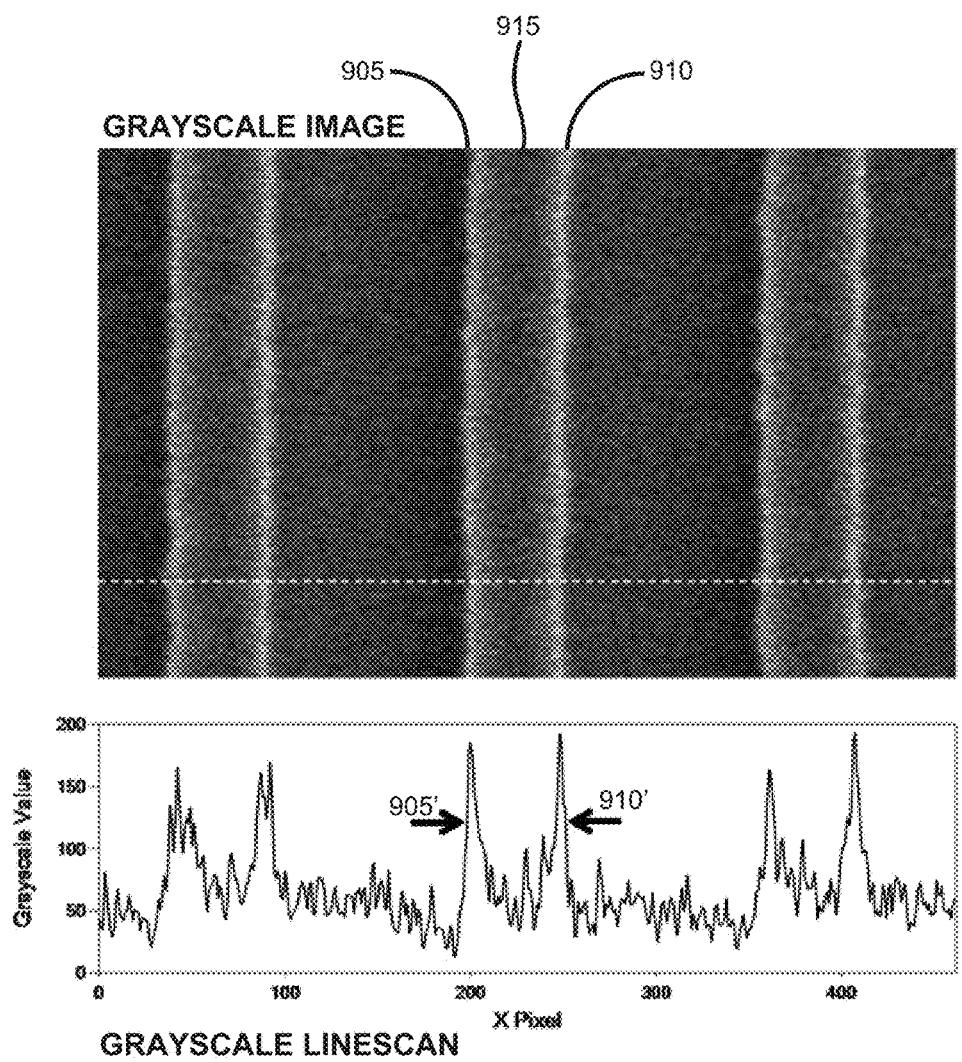

FIG. 16
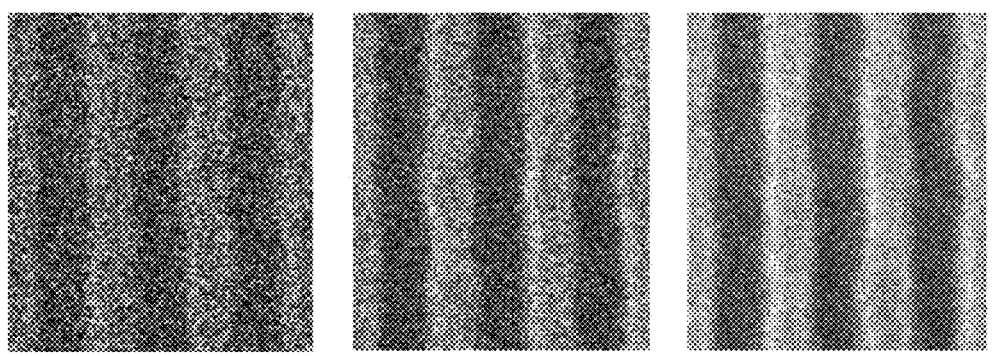
FIG. 17C
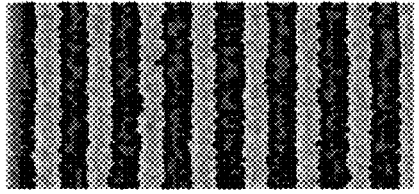
No Filter
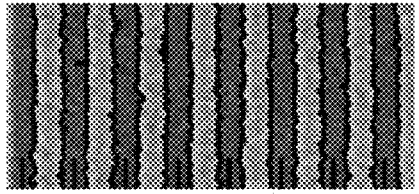
7X2 Gaussian Filter Greyscale value (vertical axis) versus horizontal position

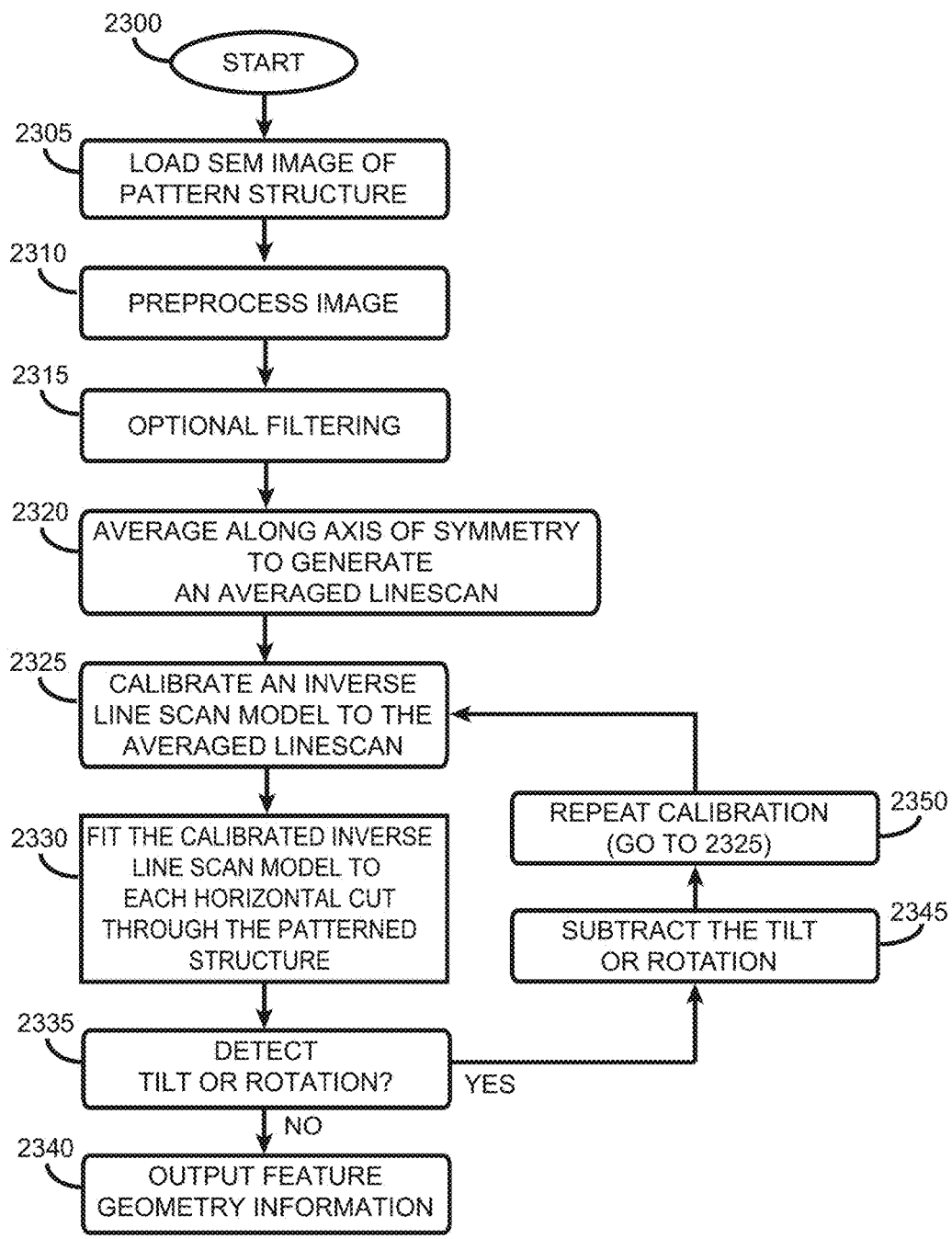

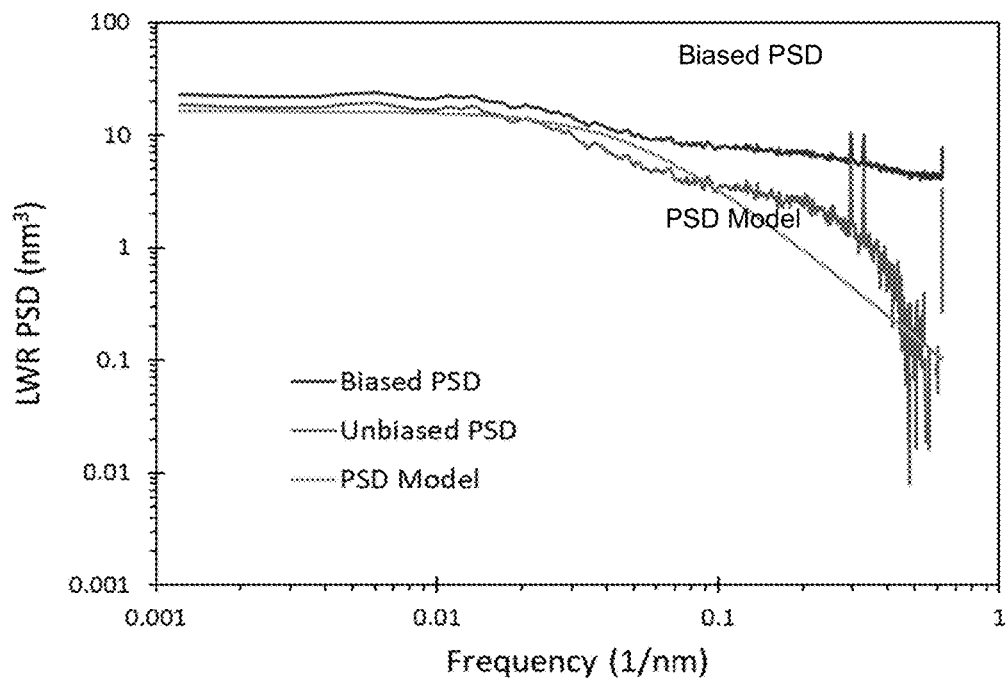
FIG. 27A ONLY WHITE NOISE SUBTRACTION
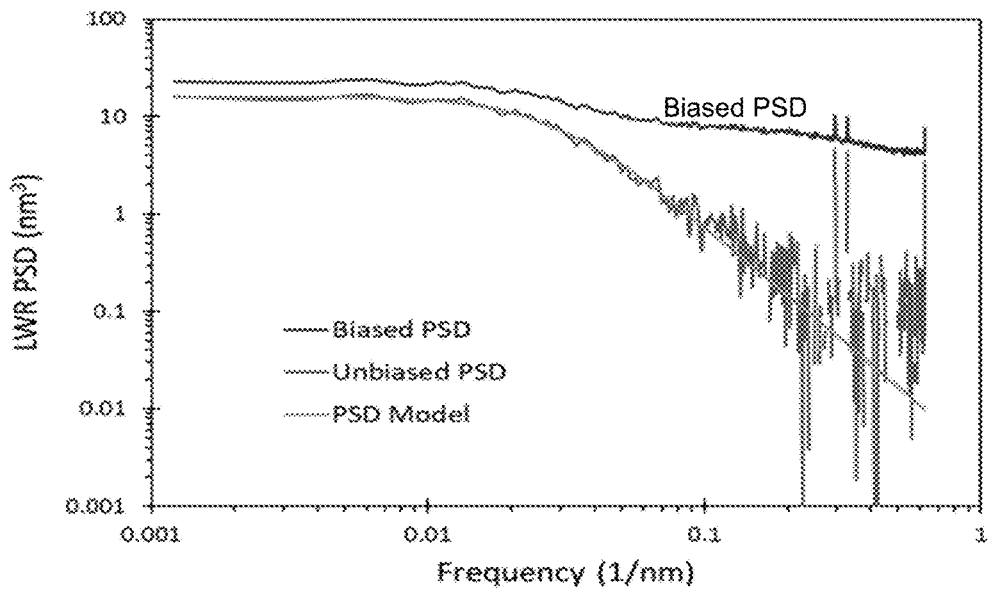
FIG. 27B PINK NOISE SUBTRACTION

SYSTEM AND METHOD FOR REMOVING NOISE FROM ROUGHNESS MEASUREMENTS

CROSS REFERENCE TO RELATED APPLICATIONS

This patent application is a continuation-in-part of and claims priority to U.S. application Ser. No. 15/892,080 filed Feb. 8, 2018 titled "Edge Detection System" (now U.S. Pat. No. 10,170,966. This application further claims priority to U.S. Provisional Patent Application No. 62/678,866 filed May 31, 2018 titled "System and Method for Removing Noise From Roughness Measurements" and U.S. Provisional Patent Application No. 62/739,721 filed Oct. 1, 2018 titled "System and Method for Generating and Analyzing Roughness Measurements." Further, as a continuation-in-part of U.S. application Ser. No. 15/892,080, this application claims priority to U.S. Provisional Patent Application Ser. No. 62/602,152, filed Apr. 13, 2017 and titled "Edge Detection System." All applications are incorporated by reference herein as if reproduced in full below.

BACKGROUND

The disclosures herein relate generally to roughness measurements of pattern structures, and more particularly, to roughness measurements of pattern structures in noise-prone images, such as in images formed when using a scanning electron microscope (SEM) or other imaging apparatus that produce images including undesired noise, and even more particularly, to removing such image noise from such roughness measurements.

BRIEF SUMMARY

Disclosed herein are systems and methods that remove noise from roughness measurements to determine roughness of a feature in a pattern structure. In one embodiment, a method for determining roughness of a feature in a pattern structure includes generating, using an imaging device, a set of one or more images. Each image of the set includes one or more instances of a feature within a respective pattern structure, and each image includes measured linescan information corresponding to the pattern structure that includes noise. The method also includes detecting edges of the features within the pattern structure of each image of the set without filtering the images, generating a biased power spectral density (PSD) dataset representing feature geometry information corresponding to the edge detection measurements of the set of images, evaluating a high-frequency portion of the biased PSD dataset to determine a noise model for predicting noise over all frequencies of the biased PSD dataset, and subtracting the noise predicted by the determined noise model from a biased roughness measure to obtain an unbiased roughness measure.

In another embodiment, a system for determining roughness of a feature in a pattern structure includes an imaging device for generating a set of one or more images, and a processor. Each image of the set includes one or more instances of a feature within a respective pattern structure, and each image includes measured linescan information corresponding to the pattern structure that includes noise. The processor is coupled to receive the measured linescan information from the imaging device. The processor is configured to detect edges of the features within the pattern structure of each image of the set without filtering the images, generate a biased power spectral density (PSD) dataset representing feature geometry information corresponding to the edge detection measurements of the set of images, evaluate a high-frequency portion of the biased PSD dataset to determine a noise model for predicting noise over all frequencies of the biased PSD dataset, and subtract the noise predicted by the determined noise model from a biased roughness measure to obtain an unbiased roughness measure.

BRIEF DESCRIPTION OF THE DRAWINGS

The appended drawings illustrate only exemplary embodiments of the invention and therefore do not limit its scope because the inventive concepts lend themselves to other equally effective embodiments.

FIG. 7 is a block diagram of a scanning electron microscope (SEM) coupled to an information handling system (IHS) that together form one embodiment of the disclosed edge detection apparatus.

FIG. 9 shows a gray scale image representation on top with a corresponding grayscale linescan along one horizontal cut being graphically plotted immediately below.

FIG. 16 shows portions of three SEM images of nominally the same lithographic features taken at different SEM electron doses.

FIG. 17C shows grayscale images as an example of using a simple threshold edge detection algorithm with image filtering in the right image, and without image filtering in the left image.

FIG. 23 is a flowchart that depicts a representative overall process flow that the disclosed SEM edge detection system employs to detect edges of a pattern structure.

FIG. 27A shows a biased PSD dataset and only white noise subtraction to generate an unbiased PSD dataset.

FIG. 27B shows a biased PSD dataset and pink noise subtraction to generate an unbiased PSD dataset.

DETAILED DESCRIPTION

Figure 1A:
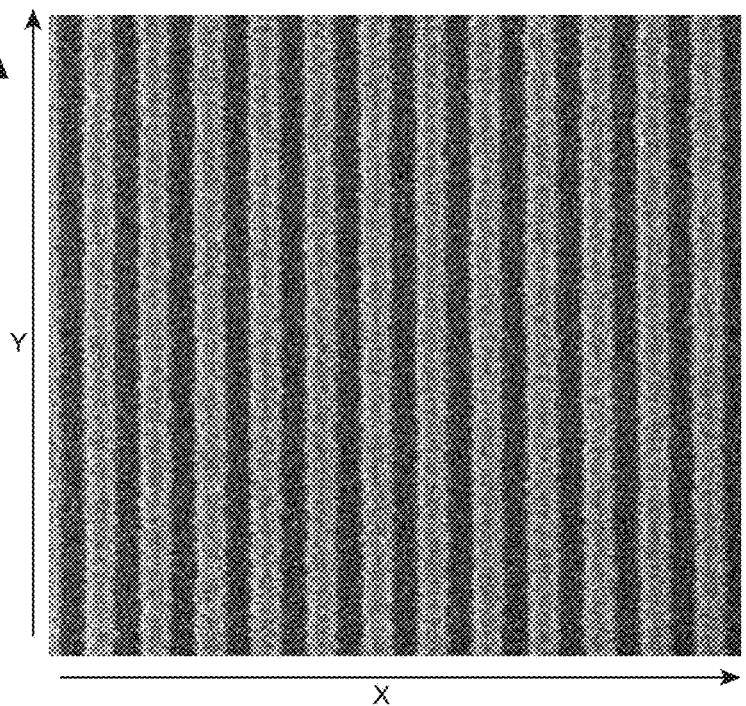
FIG. 1A is a representation of a pattern structure that exhibits parallel line features with spaces in between the lines.

Measuring the roughness of a pattern is complicated by that fact that noise in the measurement system is difficult to differentiate from the roughness being measured. It is common to using an imaging tool, such as a microscope, to create a detailed image of an object to be measured and then analyze the information on that image to measure and characterize the roughness of one or more features of the object. In this case, noise in the acquired image can appear to be roughness of the features in the image. Described below are techniques useful to separate the noise in the image from the actual roughness of the features in order to produce more accurate measurements of the roughness of the features.

As an example, scanning electron microscopes (SEMs) are very useful for studying the features of pattern structures, such as semiconductor devices, for example. Unfortunately, measuring feature roughness of these structures is often challenging because of the noise that is inherent in SEM images. Filtering (smoothing) of the SEM image is typically needed to achieve accurate edge detection, but such filtering undesirably changes the feature roughness that is measured. An edge detection approach is needed that reliably detects edges in very noisy SEM images without the use of image filtering (or at least without any filtering that would change the feature roughness that is measured).

Pattern roughness is a major problem in many fields. Many if not all techniques for creating patterns of various shapes produce roughness on the edges of those patterns, at least on the near molecular scale if not larger scales. For example, in advanced lithography for semiconductor manufacturing, especially for extreme ultraviolet (EUV) lithography but for other lithography methods as well, roughness of the printed and etched patterns can cause many negative effects. Reduction in roughness requires a better understanding of the sources of stochastic variation, which in turn requires better measurement and characterization of rough features. Prior art roughness measurement approaches suffer from severe bias because noise in the image adds to the roughness on the wafer. The disclosures herein are believed to provide the first practical approach to making unbiased roughness measurements through the use of a physics-based inverse linescan model. This enables accurate and robust measurement of roughness parameters over a wide range of SEM metrology conditions.

Before discussing embodiments of the disclosed technology that address the SEM image noise problem, this disclosure first discusses lithography of pattern structures and the frequency dependence of roughness.

1. Stochastic Effects in Lithography

Lithography and patterning advances continue to propel Moore's Law by cost-effectively shrinking the area of silicon consumed by a transistor in an integrated circuit. Besides the need for improved resolution, these lithography advances should also allow improved control of the smaller features being manufactured. Historically, lithographers focused on "global" sources of variation that affect patterning fidelity (e.g., exposure dose and focus variations, hot-plate temperature non-uniformity, scanner aberrations) by attempting to minimize the sources of these variations and by developing processes with minimum sensitivity to these variations. Today's small features, however, also suffer from "local" variations caused by the fundamental stochastics of patterning near the molecular scale.

In lithography, light is used to expose a photosensitive material called a photoresist. The resulting chemical reactions (including those that occur during a post-exposure bake) change the solubility of the resist, enabling patterns to be developed and producing the desired critical dimension (CD). For a volume of resist that is "large" (that is, a volume that contains many, many resist molecules), the amount of light energy averaged over that volume produces a certain amount of chemical change (on average) which produces a certain (average) amount of dissolution to create the pattern. The relationships between light energy, chemical concentration, and dissolution rate can be described with deterministic equations that predict outputs for a given set of inputs. These models of lithography are extremely useful and are commonly used to understand and control lithography processes for semiconductor manufacturing.

This deterministic view of a lithography process (certain inputs always produce certain outputs) is only approximately true. The "mean field theory" of lithography says that, on average, the deterministic models accurately predict lithographic results. If we average over a large number of photons, a single number for light energy (the average) is sufficient to describe the light energy. For a large volume of resist, the average concentration of a chemical species sufficiently describes its chemical state. But for very small volumes, the number of atoms or molecules in the volume becomes random even for a fixed "average" concentration. This randomness within small volumes (that is, for small quantities of photons or molecules or numbers of events) is generally referred to as "shot noise", and is an example of a stochastic variation in lithography that occurs when the region of interest approaches the molecular scale.

A stochastic process is one in which the results of the process are randomly determined. At the atomic/molecular level, essentially all processes are stochastic. For semiconductor patterning at the 20-nm node and below (with minimum feature sizes below 40 nm), the dimensions of interest are sufficiently small that stochastic effects become important and may even dominate the total variations that affect the dimensions, shapes, and placements of the patterns being fabricated. These stochastic effects can also be important for larger feature sizes under some circumstances.

Figure 1B:
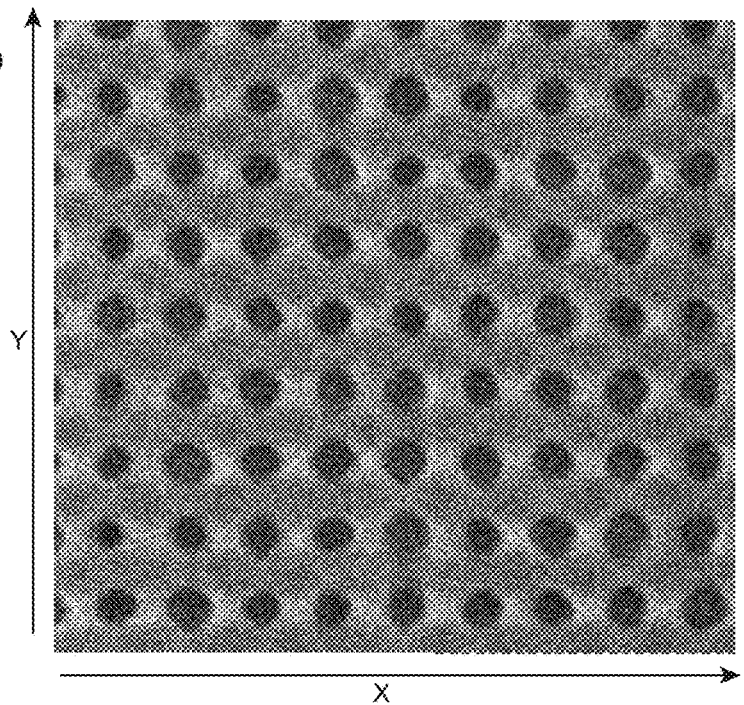
FIG. 1B is a representation of a pattern structure that includes contact hole features.

The most prominent manifestation of stochastic variations in lithography (as well as etch and other parts of the patterning process) is that the patterns being produced are rough rather than smooth (FIG. 1A). In the pattern structure shown in FIG. 1A, nominally parallel vertical lines appear as bright vertical regions, while spaces appear as dark vertical regions between the lines. The roughness of the edge of a feature is called line-edge roughness (LER), and the roughness of the width of a feature is called linewidth roughness (LWR). The roughness of the centerline of the feature (the midpoint between left and right edges) is called pattern placement roughness (PPR). Another important consequence of these stochastic variations is the random variation of the size, shape, and placement of features, which are especially evident for contact hole features (FIG. 1B).

Stochastic effects in patterning can reduce the yield and performance of semiconductor devices in several ways: a) Within-feature roughness can affect the electrical properties of a device, such as metal line resistance and transistor gate leakage; b) Feature-to-feature size variation caused by stochastics (also called local CD uniformity, LCDU) adds to the total budget of CD variation, sometimes becoming the dominant source; c) Feature-to-feature pattern placement variation caused by stochastics (also called local pattern placement error, LPPE) adds to the total budget of PPE, sometimes becoming the dominant source; d) Rare events leading to greater than expected occurrence of catastrophic bridges or breaks are more probable if error distributions have fat tails; and e) Decisions based on metrology results (including process monitoring and control, as well as the calibration of optical proximity correction (OPC) models) can be poor if those metrology results do not properly take into account stochastic variations. For these reasons, proper measurement and characterization of stochastic-induced roughness is critical.

Many other kinds of devices are also sensitive to feature roughness. For example, roughness along the edge of an optical waveguide can cause loss of light due to scattering. Feature roughness in radio frequency microelectromechanical systems (MEMS) switches can affect performance and reliability, as is true for other MEMS devices. Feature roughness can degrade the output of light emitting diodes. Edge roughness can also affect the mechanical and wetting properties of a feature in microfluidic devices. Roughness of the features in a wire grid polarizer can affect the efficiency and transmission of the polarizer.

Unfortunately, prior art roughness measurements (such as the measurement of linewidth roughness or line-edge roughness using a critical dimension scanning electron microscope, CD-SEM) are contaminated by measurement noise caused by the measurement tool. This results in a biased measurement, where the measurement noise adds to the true roughness to produce an apparent roughness that overestimates the true roughness. Furthermore, these biases are dependent on the specific measurement tool used and on its settings. These biases are also a function of the patterns being measured. Prior art attempts at providing unbiased roughness estimates often struggle in many of today's applications due to the smaller feature sizes and higher levels of SEM noise.

Thus, there is a need for a new approach to making unbiased roughness measurements that avoids the problems of prior art attempts and provides an unbiased estimate of the feature roughness that is both accurate and precise. Further, a good pattern roughness measurement method should have minimum dependence on metrology tool settings. CD-SEM settings such as magnification, pixel size, number of frames of averaging (equivalent to total electron dose in the SEM), voltage, and current may cause fairly large changes in the biased roughness that is measured. Ideally, an unbiased roughness measurement would be independent of these settings to a large degree.

2. The Frequency Dependence of Line-Edge Roughness (LER), Line-Width Roughness (LWR), and Pattern Placement Roughness (PPR)

Figure 2:
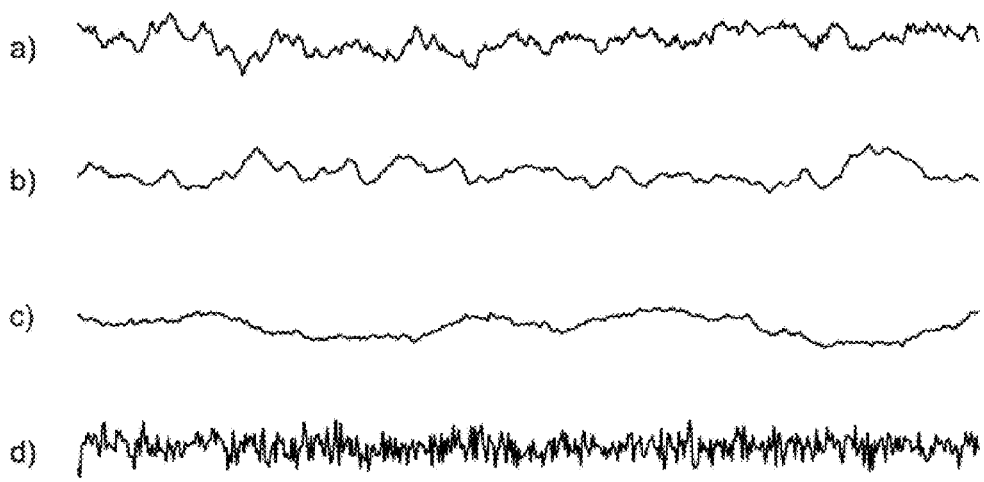
FIG. 2 shows four different rough edges, all with the same standard deviation.

Rough features are most commonly characterized by the standard deviation of the edge position (for LER), linewidth (for LWR), or feature centerline (for PPR). But describing the standard deviation is not enough to fully describe the roughness. FIG. 2 shows four different rough edges, all with the same standard deviation. The prominent differences visible in the edges make it clear that the standard deviation is not enough to fully characterize the roughness. Instead, a frequency analysis of the roughness is required. The four randomly rough edges depicted in FIG. 2 all have the same standard deviation of roughness, but differ in the frequency parameters of correlation length ($0$ and roughness exponent (H). More specifically, with respect to FIG. 2, in case a)

4=10, H=0.5; in case b) 4=10, H=1.0; in case c) 4=100, H=0.5; and in case d) 4=0.1, H=0.5.

The standard deviation of a rough edge describes its variation relative to and perpendicular to an ideal straight line. In FIG. 2, the standard deviation describes the vertical variation of the edge. But the variation can be spread out differently along the length of the line (in the horizontal direction in FIG. 2). This line-length dependence can be described using a correlation function such as the autocorrelation function or the height-height correlation function.

Figure 3:
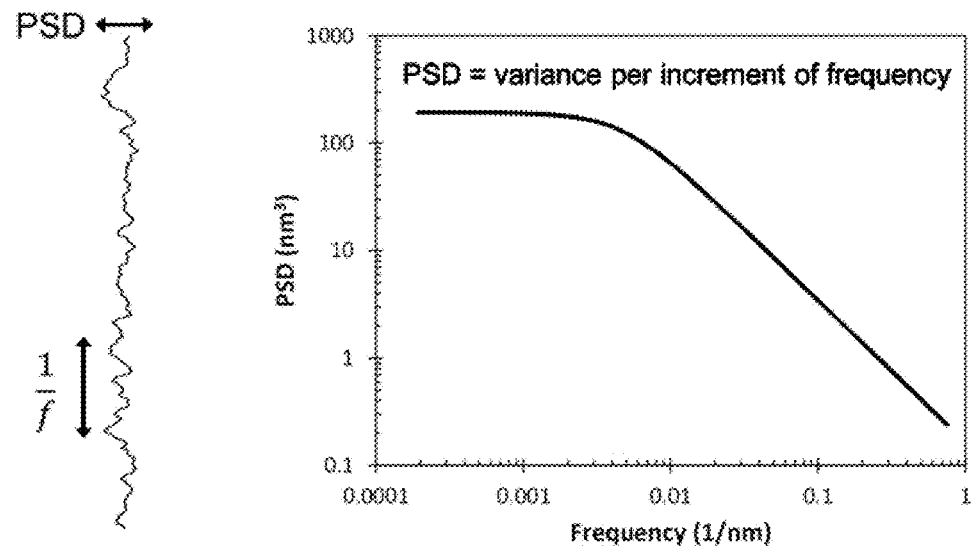
FIG. 3 is a representation of power spectral density (PSD) vs. frequency on a log-log scale.

Alternatively, the frequency f can be defined as one over a length along the line (FIG. 3). The dependency of the roughness on frequency can be characterized using the well-known power spectral density (PSD). The PSD is the variance of the edge per unit frequency (FIG. 3), and is calculated as the square of the coefficients of the Fourier transform of the edge deviation. The low-frequency region of the PSD curve describes edge deviations that occur over long length scales, whereas the high-frequency region describes edge deviations over short length scales. Commonly, PSDs are plotted on a log-log scale as used in FIG. 3.

The PSD of lithographically defined features generally has a shape similar to that shown in FIG. 3. The low-frequency region of the PSD is flat (so-called "white noise" behavior), and then above a certain frequency it falls off as a power of the frequency (a statistically fractal behavior). The difference in these two regions has to do with correlations along the length of the feature. Points along the edge that are far apart are uncorrelated with each other (statistically independent), and uncorrelated noise has a flat power spectral density. But at short length scales the edge deviations become correlated, reflecting a correlating mechanism in the generation of the roughness, such as acid reaction-diffusion for a chemically amplified resist. The transition between uncorrelated and correlated behavior occurs at a distance called the correlation length.

Figure 4:
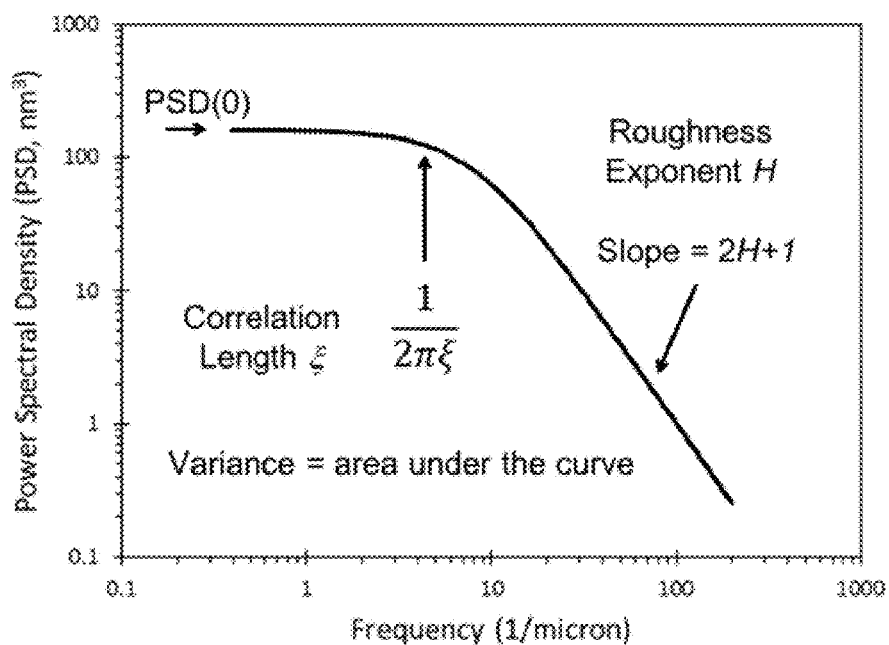
FIG. 4 is a graphic representation of power spectral density (PSD) plotted vs. frequency and depicting roughness parameters PSD(0), correlation length, and roughness exponent.

FIG. 4 shows that a typical PSD curve can be described with three parameters. PSD(0) is the zero-frequency value of the PSD. While this value of the PSD can never be directly measured (zero frequency corresponds to an infinitely long line), PSD(0) can be thought of as the value of the PSD in the flat low-frequency region. The PSD begins to fall near a frequency of $1/(2\pi\xi)$ where $\xi$ is the correlation length. In the fractal region, we have what is sometimes called "1/f" noise and the PSD has a slope (on the log-log plot) corresponding to a power of 1/f. The slope is defined as 2H+1 where H is called the roughness exponent (or Hurst exponent). Typical values of H are between 0.5 and 1.0. For example, H=0.5 when a simple diffusion process causes the correlation. Each of the parameters of the PSD curve has important physical meaning for a lithographically defined feature as discussed in more detail below. The variance of the roughness is the area under the PSD curve and can be derived from the other three PSD parameters. The exact relationship between variance and the other three PSD parameters depends on the exact shape of the PSD curve in the mid-frequency region (defined by the correlation length), but an approximate relationship can be used to show the general trend, as per EQUATION 1 below:

$$\sigma^2 \approx \frac{PSD(0)}{(2H+1)\xi} \qquad \text{EQUATION 1}$$

Figure 5:
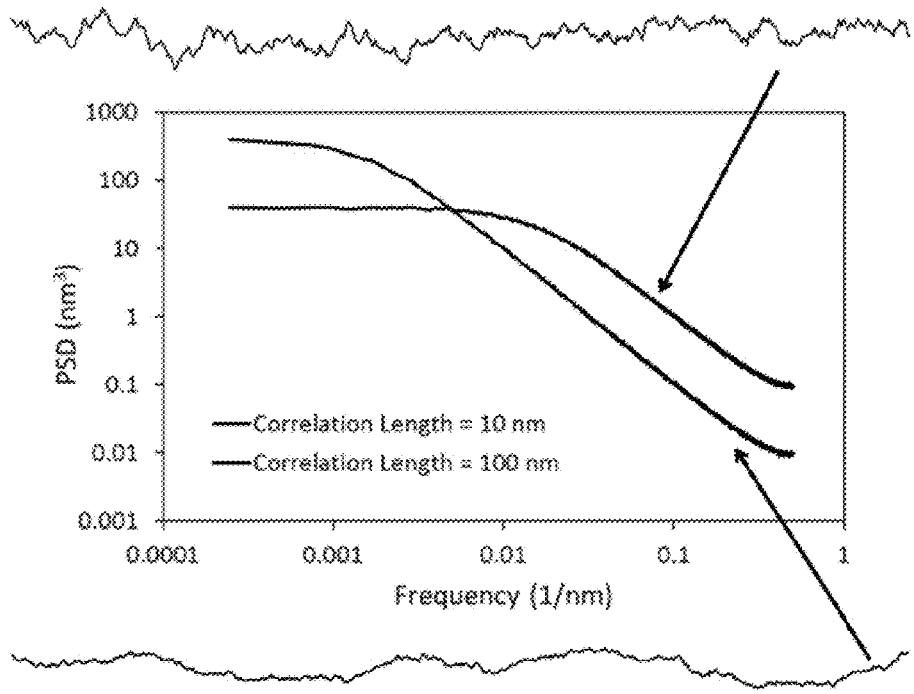
FIG. 5 shows two power spectral densities (PSDs) corresponding to respective edges of a feature on a pattern structure.

The differences observed in the respective four rough edges of FIG. 2 can now be easily seen as differences in the PSD behavior of the features. FIG. 5 shows two PSDs, corresponding to edge a) and edge c) from FIG. 2. While these two edges have the same variance (the same area under the PSD curve), they have different values of PSD(0) and correlation length (in this case the roughness exponent was kept constant). Although the standard deviations of the roughness of edge a) and edge c) are the same, these edges exhibit different PSD behaviors. As discussed below, the different PSD curves will result in different roughness behavior for lithographic features of finite length.

3. Impact of the Frequency Behavior of Roughness

The roughness of the lines and spaces of pattern structures is characterized by measuring very long lines and spaces, sufficiently long that the flat region of the PSD becomes apparent. For a sufficiently long feature the measured LWR (that is, the standard deviation 6 of the measured linewidths along the line) can be thought of as the LWR of an infinitely long feature, $\sigma_{LWR}(\infty)$. But pattern structures such as semiconductor devices are made from features that have a variety of lengths L. For these shorter features, stochastics will cause within-feature roughness, $\sigma_{LWR}(L)$, and feature-to-feature variation described by the standard deviation of the mean linewidths of the features, $\sigma_{CDU}(L)$. This feature-to-feature variation is called the local critical dimension uniformity, LCDU, since it represents CD (critical dimension) variation that is not caused by the well-known "global" sources of error (scanner aberrations, mask illumination non-uniformity, hotplate temperature variation, etc.).

For a line of length L, the within-feature variation and the feature-to-feature variation can be related to the LWR of an infinitely long line (of the same nominal CD and pitch) by the Conservation of Roughness principle given in EQUATION 2 below:

$$\sigma_{CDU}^2(L) + \sigma_{LWR}^2(L) = \sigma_{LWR}^2(\infty) \qquad \text{EQUATION 2}$$

The Conservation of Roughness principle says that the variance of a very long line is partitioned for a shorter line into within-feature variation and feature-to-feature variation. How this partition occurs is determined by the correlation length, or more specifically by $L/\xi$. Using a basic model for the shape of the PSD as an example, it is seen that:

$$\sigma_{CDU}^2(L) = \frac{PSD(0)}{L}\left[1 - \frac{\xi}{L}(1 - e^{-L/\xi})\right] \qquad \text{EQUATION 3}$$

Thus, EQUATIONS 1-3 show that a measurement of the PSD for a long line, and its description by the parameters PSD(0), $\xi$, and H, enables one to predict the stochastic influence on a line of any length L. It is noted that the LCDU does not depend on the roughness exponent, making H less important than PSD(0) and $\xi$. For this reason, it useful to describe the frequency dependence of roughness using an alternate triplet of parameters: $\sigma_{LWR}(\infty)$, PSD(0), and $\xi$. Note that these same relationships apply to LER and PPR as well.

It is also noted that, examining EQUATION 3, the correlation length is the length scale that determines whether a line of length L acts "long" or "short". For a long line, $L \gg \xi$ and the local CDU behaves as per EQUATION 4 below:

$$\sigma_{CDU}(L) \approx \sqrt{\frac{PSD(0)}{L}} \quad \text{when } L \gg \xi \qquad \text{EQUATION 4}$$

This long-line result provides a useful interpretation for PSD(0): It is the square of the LCDU for a given line times the length of that line. Reducing PSD(0) by a factor of 4 reduces the LCDU by a factor of 2, and the other PSD parameters have no impact (so long as L$\gg\xi$). Typically, resists have yielded correlation lengths on the order of one quarter to one half of the minimum half-pitch of their lithographic generation. Thus, when features are longer than approximately five times the minimum half-pitch of the technology node, we are generally in this long line length regime. For shorter line lengths, the correlation length begins to matter as well.

Figure 6:
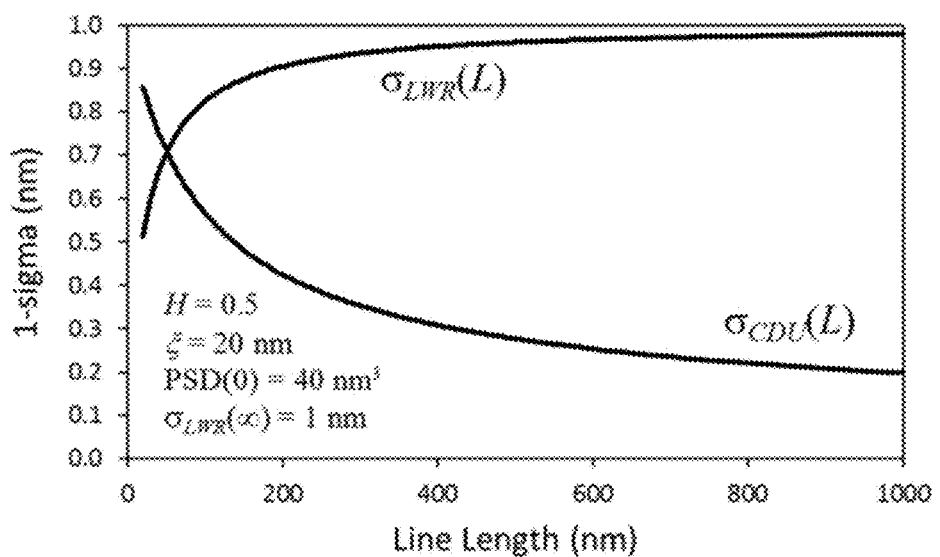
FIG. 6 is a graphic representation of the tradeoff of within-feature variation and feature-to-feature variation as a function of line length.

EQUATIONS 1-3 show a trade-off of within-feature variation and feature-to-feature variation as a function of line length. FIG. 6 shows an example of this relationship. For very long lines, LCDU is small and within-feature roughness approaches its maximum value. For very short lines the LCDU dominates. However, due to the quadratic nature of the Conservation of Roughness, $\sigma_{LWR}(L)$ rises very quickly as L increases, but LCDU falls very slowly as L increases. Thus, there is a wide range of line lengths where both feature roughness and LCDU are significant.

Since the Conservation of Roughness principle applies to PPR as well, short features suffer not only from local CDU problems but also from local pattern placement errors (LPPE) as well. For the case of uncorrelated left and right edges of a feature, the PSD(0) for LWR is typically twice the PSD(0) of the LER. Likewise, the PSD(0) of the LER is typically twice the PSD(0) of the PPR. Thus, in general, the LPPE is about half the LCDU. When left and right feature edges are significantly correlated, these simple relationships no longer hold.

4. Measurements of the Roughness of Pattern Structures with a Scanning Electron Microscope (SEM)

A common way to measure feature roughness for small features is the top-down critical dimension scanning electron microscope (CD-SEM). Typical light microscopes have magnifications up to 1000× and resolutions down to a few hundred nanometers. Scanning electron microscopes use electrons to create very small spots (near 1 nm in width) that can be used to create high-resolution images, with magnifications above 20,000×. CD-SEMs are SEMs that have been optimized for measuring the dimensions of a wide range of features found on semiconductor wafers. They can measure the mean critical dimension of a rough feature with high precision, but have also proven very useful for measuring LER, LWR, PPR, and their PSDs as well. However, there are errors in the SEM images that can have large impacts on the measured roughness and the roughness PSD while having little impact on the measurement of mean CD. For this reason, the metrology approach needed for PSD measurement may be quite different than the approach commonly used for mean CD measurement.

FIG. 7 shows a block diagram of one embodiment of the disclosed measurement system 700 that determines feature roughness. The pattern structure sample 800 and the electron imaging optics (710, 715, 720, 725) are situated in a vacuum chamber 701 that is evacuated by vacuum pump 702. Electrons are generated from a source such as an electron gun 705 to form an electron beam 707. Common electron beam sources include a heated tungsten filament, a lanthanum hexaboride (LaB6) crystal formed into a thermionic emission gun, or a sharp-tipped metal wire formed to make a field emission gun. The emitted electrons are accelerated and focused using electromagnetic condenser lenses 710, 715, and 720. The energy of the electrons striking the pattern structure sample 800 is generally in the 200 eV to 40 keV range in SEMs, but more typically 300 eV to 800 eV for CD-SEMs. Final condenser lens 720 employs scanning coils 725 to provide an electric field that deflects electron beam 707 toward pattern structure 800 as a focused spot. Scanning coils 725 scan the focused spot across the pattern structure 800 through final lens aperture 735 in a raster scan fashion to expose a specific field of view on the pattern structure 800. SEM 701 includes a backscatter electron detector 740 that detects backscatter electrons scattering back from pattern structure sample 800. SEM 700 also includes a secondary electron detector 745, as shown in FIG. 7. Prior to imaging pattern structure 800, the user places pattern structure 800 on a pattern structure receiver 732 that supports and positions pattern structure 800 within SEM 700. SEM 700 includes a controller (not shown) that controls the raster scanning of pattern structure 800 during imaging.

Figure 8A:
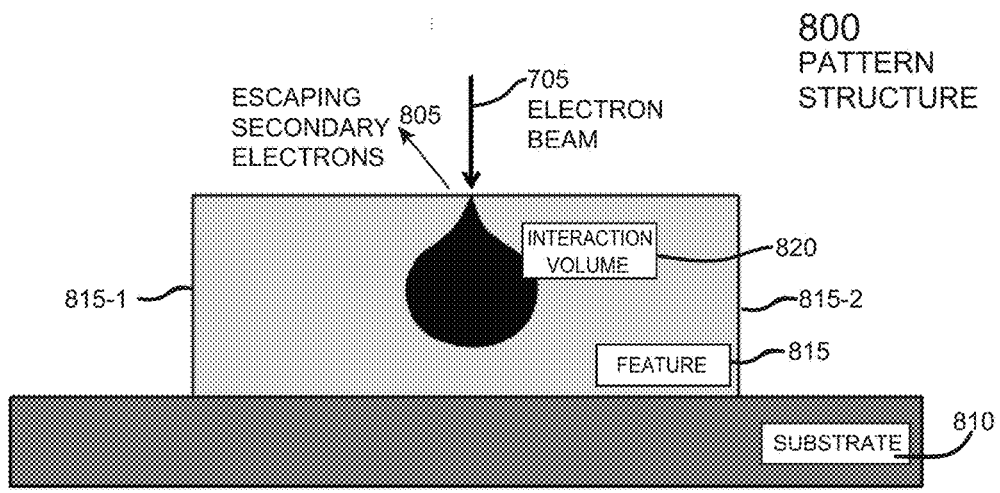
FIG. 8A is a representation of a feature disposed on a substrate that depicts an electron beam impinging on the center of the feature.
Figure 8B:
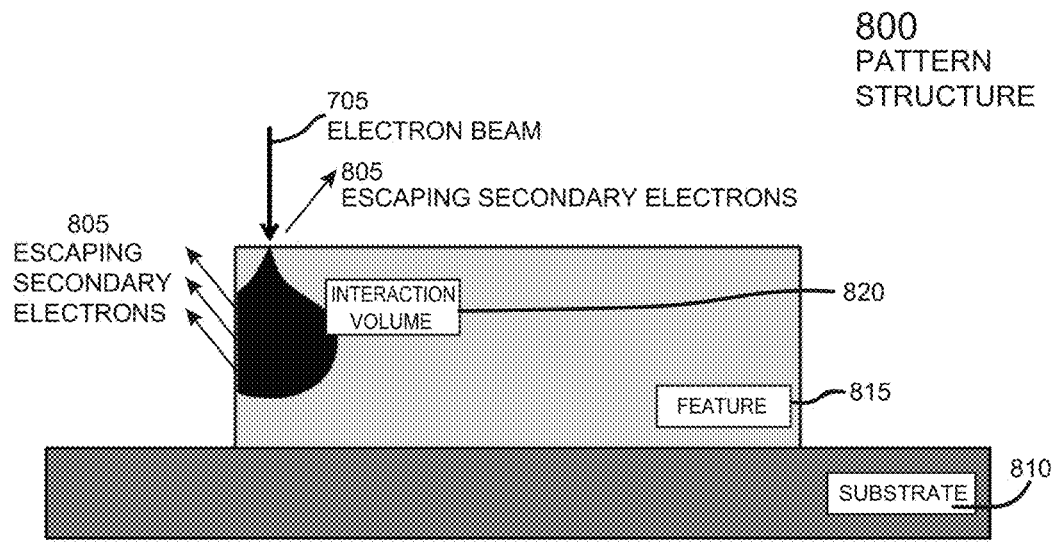
FIG. 8B is a representation of a feature disposed on a substrate that depicts an electron beam impinging on the feature near its edge.

Referring now to FIGS. 8A and 8B, the electrons of electron beam 705 that strike pattern structure sample 800 undergo a number of processes that depend on the energy of the electron and the material properties of the sample. Electrons scatter off the atoms of the sample material, release energy, change direction, and often generate a cascade of secondary electrons by ionizing the sample atoms. Some of these secondary electrons may escape from the pattern structure (805) and others may remain inside the pattern structure. Pattern structure 800 includes a substrate 810, such as a semiconductor wafer. A feature 815 is disposed atop substrate 810, as shown in FIG. 8A. Feature 815 may be a metallic line, a semiconductor line, a photoresist line or other structures on substrate 810. Feature 815 may have other shapes such as a pillar or a hole, or more complicated shapes. Feature 815 may be repeating or isolated with respect to other features on the pattern structure. The space surrounding feature 815 may be empty (vacuum or air) or may be filled with a different material. Pattern structure 800 may be a liquid crystal or other flat panel display, or other pattern semiconductor or non-semiconductor device. Feature 815 includes edges 815-1 and 815-2. The region of feature 815 where electron beam 705 interacts with feature 815 is the interaction volume 820 that exhibits, for example, a tear-droplet-like shape as depicted in FIG. 8A.

Occasionally electrons ricochet backwards off the atom nucleus and exit out of the sample (called backscatter electrons). Some of the lower energy secondary electrons can also escape out of the sample 805 (frequently through the edges of a feature, see FIG. 8B). The way in which a SEM forms an image is by detecting the number of secondary electrons and/or backscatter electrons that escape the sample for each beam position.

As the electron beam is scanned across pattern structure sample 800 during one linescan, it "dwells" at a specific spot for a specific time. During that dwell time, the number of electrons detected by either the backscatter detector 725 or secondary electron detector 740, or both, is recorded. The spot is then moved to the next "pixel" location, and the process is repeated. The result is a two-dimensional array of pixels (locations along the surface of the sample) with detected electron counts digitally recorded for each pixel. The counts are typically then normalized and expressed as an 8-bit grayscale value between 0 and 255. This allows the detected electron counts to be plotted as a grayscale "image", such as those images shown in FIG. 1. While the image coming from a SEM reminds a viewer of an optical image as perceived through the eye, it is important to note that these grayscale images are actually just convenient plots of the collected data.

A CD-SEM measures the width of a feature using the SEM image. The first step in measuring feature width is to detect the edges of the features. For pixels near an edge of a feature, higher numbers of secondary electrons escape through the feature edge, producing bright pixels called "edge bloom" (see FIG. 8B and FIG. 9). It is this bright edge bloom that allows the feature edge to be detected. For example, in the grayscale image representation in the upper portion of FIG. 9, such edge blooms are observed at edges 905 and 910 of feature 915. A linescan is essentially a horizontal cut through a 2D SEM image that provides a grayscale value as a function of horizontal pixel position on the feature, as in the graph shown in the bottom half of FIG. 9.

The data from a single horizontal row of pixels across the sample is called a "linescan". Note that the term linescan is used here broadly enough to include cases where an image is formed without the use of scanning. The positions of the edges of a feature can be detected from a single linescan, or from a collection of linescans representing the entire image, such as shown in the upper portion of FIG. 9. These same edges appear as peaks 905' and 910' in the grayscale value vs. pixel position graph in the lower portion of FIG. 9. Once the edges of a particular feature have been determined, the width of the particular feature is the difference between the positions of these two edges.

5. Linescan Models

Images are created through a physical process based on the microscope or other imaging tool used to acquire the image of a structure. Often these images are two-dimensional arrays of data, where the image can be thought of as a data set derived from the structure. A single one-dimensional cut through the image is called a linescan. A model of the imaging tool can predict the image for a given structure being imaged. For example, a model that describes a scanning electron microscope could predict the image that would be obtained by a SEM when imaging a given structure.

A CD-SEM converts a measured linescan or a series of measured linescans into a single dimension number, the measured CD. To better understand how the linescan relates to the actual dimensions of the feature being measured, it is important to understand how the systematic response of the SEM measurement tool to pattern structures manifests the shape of the resulting linescan. Rigorous 3D Monte Carlo simulations of SEM linescans can be extremely valuable for this purpose, but they are often too computationally expensive for day-to-day use. Thus, one approach is to develop a simplified analytical linescan model (ALM) that is more computationally appropriate to the task of quickly predicting linescans. The ALM employs the physics of electron scattering and secondary electron generation, and each term in the model has physical significance. This analytical linescan expression can be fit to rigorous Monte Carlo simulations to both validate and calibrate its use.

The general application for the ALM has been the typical forward modeling problem: Given material properties (for the feature and the substrate) and a geometric description of the feature (width, pitch, sidewall angle, top corner rounding, footing, etc.), the ALM predicts the linescan that would result. The mathematical details of the ALM are found in the publications: Chris A. Mack and Benjamin D. Bunday, "Analytical Linescan Model for SEM Metrology", *Metrology, Inspection, and Process Control for Microlithography XXIX*, Proc., SPIE Vol. 9424, 94240F (2015), and Chris A. Mack and Benjamin D. Bunday, "Improvements to the Analytical Linescan Model for SEM Metrology", *Metrology, Inspection, and Process Control for Microlithography XXX*, Proc., SPIE Vol. 9778, 97780A (2016), the disclosures of both publications being incorporated herein by reference in their entireties. Other models with similar inputs and outputs can also be used.

The analytical linescan model (ALM) is briefly reviewed below. The mathematical modeling begins by assuming the interaction of the electron beam with a flat sample of a given substance produces an energy deposition profile that takes the form of a double Gaussian, with a forward scattering width and a fraction of the energy forward scattered, and a backscatter width and a fraction of the energy deposited by those backscattered electrons. The model also assumes that the number of secondary electrons that is generated within the material is in direct proportion to the energy deposited per unit volume, and the number of secondary electrons that escape the wafer (and so are detected by the SEM) are in direct proportion to the number of secondary electrons near the very top of the wafer.

The secondary electrons that reach the detector will emerge some distance r away from the position of the incident beam. From the assumptions above, the number of secondary electrons detected will be a function as given in EQUATION 5.

$$f(r) = ae^{-r^2/2\sigma_f^2} + be^{-r^2/2\sigma_b^2} \qquad \text{EQUATION 5}$$

where $\sigma_f$ and $\sigma_b$ are the forward and backscatter ranges, respectively, and a and b are the amounts of forward scattering and backscattering, respectively.

Figure 10:
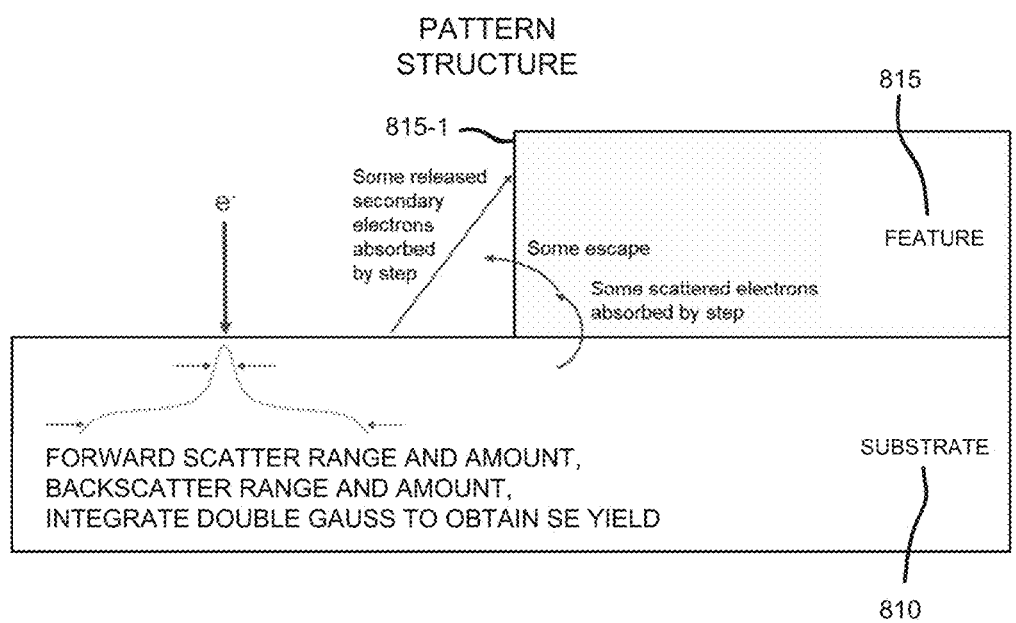
FIG. 10 shows an example of a pattern structure including a feature situated atop a substrate with varying numbers of electrons escaping from the pattern structure depending on where the electron beam impinges on the pattern structure.

SEMs detect topography because of the different number of secondary electrons that escape when the beam is in the space between features compared to when the beam is on top of the feature. FIG. 10 shows that secondary electrons have trouble escaping from a space (especially if it is small), making spaces appear relatively dark. When an electron beam is focused to a spot in a space between lines, scattered electrons interact with feature 815 which absorbs some of the escaping secondary electrons. The detected secondary electron signal is reduced as the beam approaches the feature edge within the space.

The absorption by the step (i.e. feature 815) can be modeled to produce a prediction of the shape of the linescan in the space region. If a large feature has a left edge 815-1 at x=0, with the feature 815 to the right (positive x), the detected secondary electron signal as a function of position (SE(x)) will be given by EQUATION 6 below:

$$\text{For } x < 0, \; \frac{SE(x)}{SE(-\infty)} = 1 - \alpha_f e^{x/\sigma_f} - \alpha_b e^{x/\sigma_b} \qquad \text{EQUATION 6}$$

where $\alpha_f$ is the fraction of forward scatter secondary electrons absorbed by the step and $\alpha_b$ is the fraction of backscatter secondary electrons absorbed by the step.

However, when the beam is on top of feature 815, the interaction of the scattered electrons with the feature is very different, as accounted for in EQUATION 7 below. As illustrated in FIG. 8, two phenomena occur as when the beam is closer to the edge compared to further away. First, secondary electrons from both forward and backscattered electrons can more easily escape out of the edge 815-1. This causes the edge bloom already discussed above. To account for this effect, a positive term $\alpha_e e^{-x/\sigma_e}$ is added to account for the enhanced escape of forward-scattered secondary electrons where $\sigma_e$ is very similar to the forward scatter range of the step material. Additionally, the interaction volume itself decreases when the beam is near the edge 815-1, so that there are fewer secondary electrons being generated. Thus, the term $\alpha_v e^{-x/\sigma_v}$ where $\sigma_v < \sigma_e$ is subtracted to give EQUATION 7 below which is the linescan expression for the top of the large feature 815:

$$\text{For } x < 0, \quad \frac{SE(x)}{SE(\infty)} = 1 + \alpha_e e^{x/\sigma_e} - \alpha_v e^{-x/\sigma_v} \quad \text{EQUATION 7}$$

Figure 11:
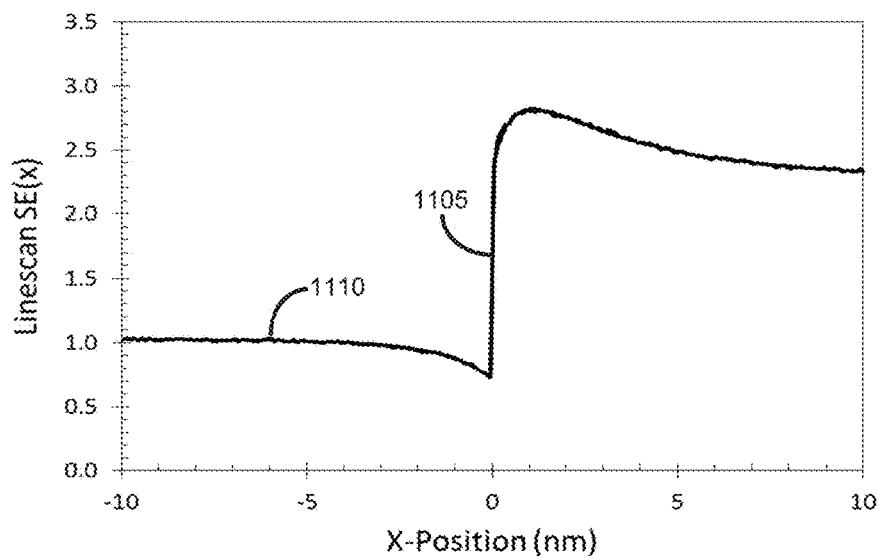
FIG. 11 shows a predicted linescan of a resist step on a pattern structure such as a silicon wafer.

FIG. 11 shows an example of the result for this model. More specifically, FIG. 11 shows a predicted linescan of a left-facing resist step 815 (large feature with left edge 815-1 at x=0) on a substrate such as a silicon wafer. The calibrated model 1105 is superimposed on the rigorous Monte Carlo simulation results 1110. The calibrated model 1105 agrees so closely with the Monte Carlo simulation results 1110 that the two curves appear together almost as one line.

The above discussion involves modelling an isolated left-facing edge 815-1. Adapting the model to include a right-facing edge involves translating and reversing the edge and adding the resulting secondaries (i.e., secondary electrons). Some complications arise if the two edges are close enough to interact, resulting in additional terms. Additionally, the impact of non-vertical sidewalls and rounded corners at the top and bottom of the feature edge may be included in the model (FIG. 12).

Figure 12:
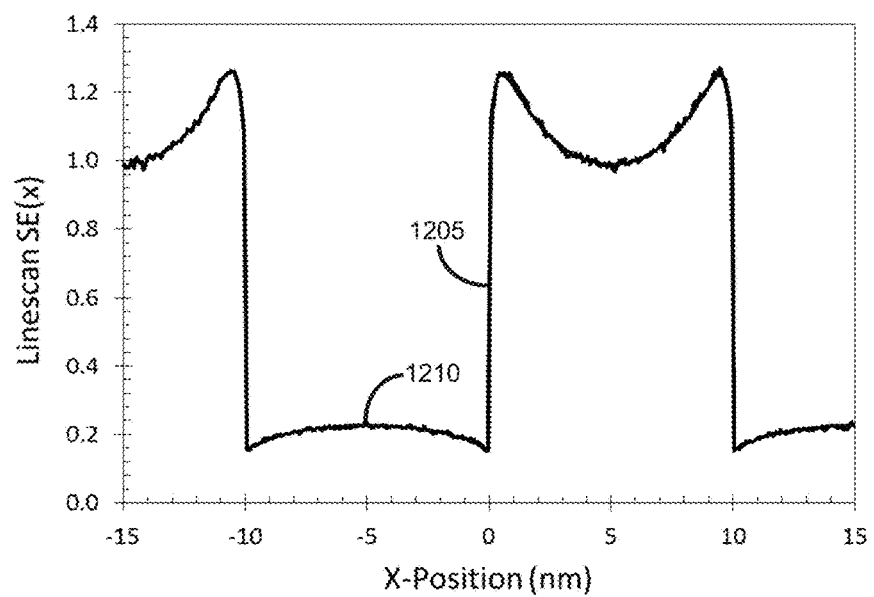
FIG. 12 shows another representative predicted linescan of a pattern of resist lines and spaces on a silicon wafer.

FIG. 12 shows a representative predicted linescan of a pattern of resist lines and spaces on a silicon wafer. The calibrated model 1205 is superimposed on the rigorous Monte Carlo simulation results 1210. Again, the calibrated model 1205 agrees so closely with the Monte Carlo simulation results 1110 that the two curves appear together almost as one line. A final model (ALM) includes 15 parameters that depend on the properties of the materials of the wafer and feature, and the beam voltage. To validate the model and to calibrate these parameters, rigorous first principle Monte Carlo simulations can be used to generate linescans for different materials and feature geometries. The ALM can then be fit to the Monte Carlo results, producing best-fit values of the 15 unknown parameters.

6. Inverse Linescan Model

Linescan or image models, such as the analytical linescan model (ALM) discussed above, predict an image or the shape of an image linescan for a particular pattern structure (such as a feature on a wafer). The ALM solves a forward modelling problem wherein the model receives geometry information for the particular feature as input, and provides the predicted shape of a respective SEM linescan of the particular feature as output.

In contrast to ALM, the disclosed edge detection system 700 includes a reverse model that receives as input "measured linescan information" from SEM 701 that describes a particular feature on the wafer. In response to the measured linescan information describing the particular feature, edge detection system 700 employs its reverse model to generate as output "feature geometry information" that describes the feature geometry that would produce the measured linescan. Advantageously, edge detection system 700 has been found to be effective even when the measured linescan information from SEM 701 includes a significant amount of image noise. In one embodiment, the outputted feature geometry information includes at least feature width. In another embodiment, the outputted feature information includes feature width and/or other geometry descriptors relative to the geometry of the particular feature, such as sidewall angle, feature thickness, top corner rounding, or bottom footing. It is noted that a feature disposed on a semiconductor wafer is an example of one particular type of pattern structure to which the disclosed technology applies.

Like many models of imaging systems, the ALM is inherently nonlinear. To address the nonlinear nature of the ALM, edge detection system 700 numerically inverts the ALM or a similar forward model and fits the resulting inverse linescan model to a measured linescan to detect feature edges (e.g. to estimate the feature geometry on the wafer). The disclosed edge detection system apparatus and edge detection process include the ability to detect and measure feature roughness. The disclosed apparatus and methodology may apply as well to other applications in general CD metrology of 1D or 2D features, such as the precise measurement of feature width (CD) and edge position or placement.

It is first noted that the ALM (and similar models as well) has two types of input parameters, namely material-dependent parameters and geometry parameters. Material-dependent parameters include parameters such as forward and backscatter distances, while geometry parameters include parameters such as feature width and pitch. In one embodiment, for a repeated edge detection application, the material parameters will be fixed and only the geometry parameters will vary. In the simplest case (that is, for simple edge detection), it is assumed that only the edge positions for the feature are changing, such that sidewall angle, corner rounding, etc., are assumed to be constant. Thus, the use of a linescan model for edge detection in edge detection system 700 involves two steps: 1) calibrating the parameters that are assumed to be constant across the entire image, and then 2) finding the feature edge positions that provide a best fit of the measured linescan to the linescan model for each measurement.

In one embodiment, in the first step, calibration is accomplished by comparing the linescan model to rigorous Monte Carlo simulations. The goal in this step is to find material parameters over the needed range of applications, and to ensure the fitting is adequate for the needed range of feature geometries. When finished, this calibrated linescan model can serve as the starting point for the generation of an inverse linescan model. The Inverse Linescan Model (ILM) should be calibrated to the specific SEM images that are to be measured. Since image grayscale values are only proportional to secondary electron signals, at the very least a mapping to grayscale values is required. In real-world applications, material properties in the experimental measurement will not be identical to those assumed in the Monte Carlo simulations such that some calibration of those parameters will also be required.

7. Calibration of the Inverse Linescan Model

Before using the ILM for edge detection, the ILM is first calibrated. Some parameters of the model (such as material-dependent parameters) are assumed to be constant for the entire image. However, geometry parameters, such as the positions of the edges, feature width and pitch, are assumed to vary for every linescan. The goal of ILM calibration is to determine the parameters that are constant for the whole image, regardless of the exact positions of the feature edges. It is a further goal of ILM calibration to accurately determine these parameters in the presence of image noise. These goals are accomplished by averaging along an axis of symmetry for the feature being measured, thus averaging out both the image noise and the actual feature roughness.

By averaging the linescan along an axis of symmetry (such as the direction parallel to a long line or space feature), information about the actual edge positions is lost, but information about the material parameters of the linescan model remain. Further, noise in the image is mostly averaged out in this way. Calibrating the ILM to the average linescan produces a set of material parameters (or any parameters assumed constant throughout the image) specific to this image.

Many features to be measured exhibit an axis of symmetry appropriate for ILM calibration. For example, a vertical edge has a vertical axis of symmetry. Averaging all pixels in a vertical column of pixels from the image will average away all vertical variation, leaving only horizontal information, in a direction perpendicular to the edge of the feature. The result of this averaging is a one-dimensional linescan called the average linescan. Likewise, a nominally circular contact hole or pillar is ideally radially symmetric. Averaging through polar angle about the center of the feature will produce an average linescan that removes noise and roughness from the image. An elliptical hole shape can also be so averaged by compressing or expanding the pixel size in one direction in proportion to the ratio of major to minor axes of the ellipse. Other axes of symmetry exist for other features as well.

One measured image (for example, one SEM image) may contain one or more features in the image. For example, FIG. 1A shows multiple vertical line features and multiple vertical space features. FIG. 1B shows multiple contact holes. For such a case, each feature can be separately averaged along an axis of symmetry to form an average linescan for that feature. For the example of FIG. 1A, the SEM image can be partitioned into vertical stripes, each stripe containing only one line feature, where the stripe extends horizontally from approximately the center of one space to approximately the center of the next space. For the example of FIG. 1B, the image can be partitioned into separate rectangular regions, each containing exactly one contact hole with the center of the contact hole approximately coinciding with the center of the rectangular region. The averaged linescan for that contact hole is then determined from that rectangular region of the image. Alternately, each of the averaged linescans from each feature in an image can themselves be averaged together to form a single averaged linescan applicable to the entire image.

For a repeated edge detection application (such as the detection of all the edges on a single SEM image), the material parameters will be fixed and only the geometry parameters will vary. In the simplest case (that is, for simple edge detection), one can assume that only the edge positions for the feature are changing, so that feature thickness, sidewall angle, corner rounding, etc., are assumed constant. Thus, the use of the ILM for edge detection will involve two steps: calibrating one time for the parameters that are assumed to be constant (i.e., material and fixed geometry properties) using the average linescan, and then finding the feature edge positions that provide a best fit of the measured linescan to the linescan model for each linescan. Optionally, calibration is first accomplished by comparison of the linescan model to rigorous Monte Carlo simulations, as has been previously described. The goal of this initial step is to find material parameters over the needed range of applications, and to ensure the model is adequate for the needed range of feature geometries. When finished, this partially calibrated linescan model must still be fully calibrated to the specific SEM images that are to be measured using the average linescan.

Figure 13A:
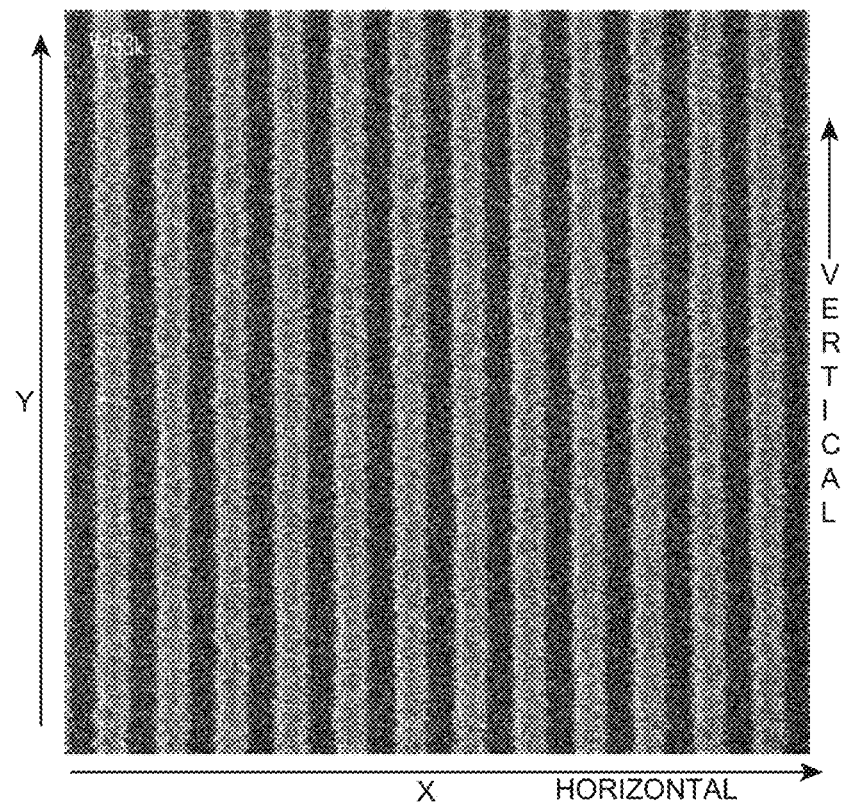
FIG. 13A is an original SEM image of a pattern structure without using the disclosed edge detection apparatus and method.
Figure 13B:
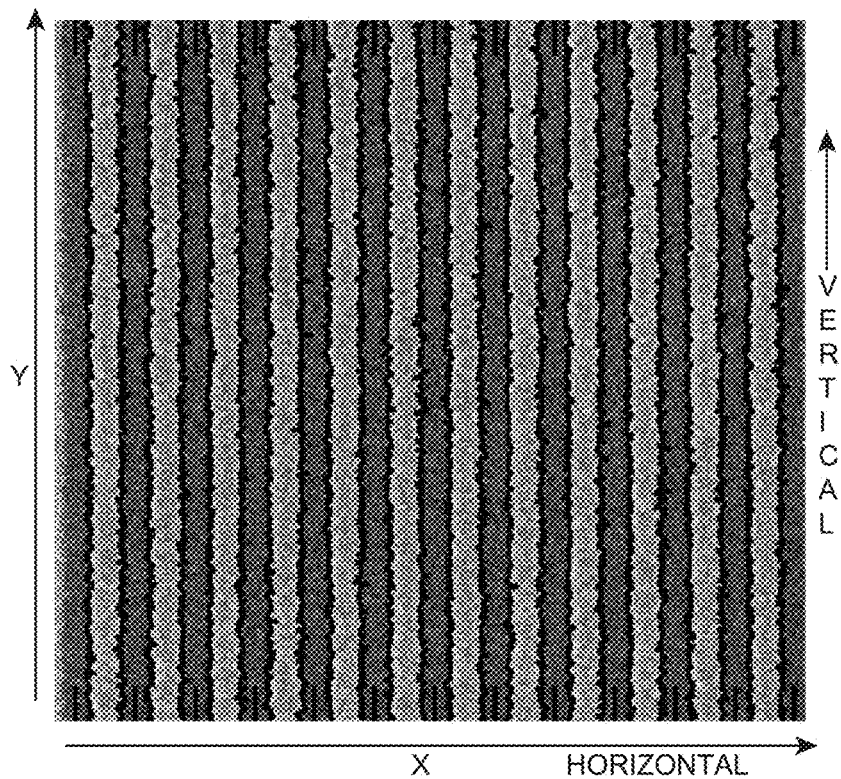
FIG. 13B is the same SEM image as FIG. 13A except using the disclosed edge detection apparatus and method.

Once the ILM has been calibrated to the given SEM image or sets of images, it is then used to detect edges. Due to the non-linear nature of linescan models such as the ALM model, numerical inversion is needed, for example using non-linear least-square regression to find the values of the left and right edge positions that best fit the model to the data. For simpler linescan models, a linear least-squares fit may be possible. Other means of "best fit" are also known in the art. The ILM as an edge detector allows the detection of edges in a high noise environment without the use of filters. FIGS. 13A and 13B demonstrate the reliable detection of edges for a very noisy image without the use of any filtering or image smoothing. More particularly, FIG. 13A is an original SEM image of a pattern structure that exhibits 18 nm lines and spaces before edge detection with an ILM. FIG. 13B is the same image after edge detection using an ILM.

Gaussian filters are common image smoothing filters designed to reduce noise in an image. Other filters such as box filters and median filters are also commonly used for this purpose. To illustrate the impact of image filtering on roughness measurement, TABLE 1 below shows the measured 3σ linewidth roughness (LWR) as a function of Gaussian filter x- and y-width (in pixels). For each case, the ILM edge detection method was used, so that the difference in the resulting LWR is only a function of the image filter parameters. The range is almost a factor of two, showing that many different roughness measurements can be obtained based on the arbitrary choice of filter parameters. In all cases, the ILM edge detection was used. If a conventional threshold edge detection method is used, the range of resulting 3σ roughness values is much greater (TABLE 2). Similar results are obtained if other filter types (box or median, for example) are used.

TABLE 1

The raw (biased) 3σ LWR (nm) as a function of Gaussian filter x- and y-width (in pixels), using ILM edge detection.

|  | y-width = 1 | y-width = 2 | y-width = 3 | y-width = 4 |
| --- | --- | --- | --- | --- |
| x-width = 1 | 4.99 | 4.67 | 4.03 | 3.82 |
| x-width = 3 | 4.92 | 4.02 | 3.48 | 3.28 |
| x-width = 5 | 4.85 | 3.82 | 3.28 | 3.00 |
| x-width = 7 | 4.79 | 3.69 | 3.13 | 2.84 |
| x-width = 9 | 4.73 | 3.59 | 3.08 | 2.80 |
| x-width = 11 | 4.68 | 3.54 | 3.07 | 2.80 |

TABLE 2

The raw (biased) 3σ LWR (nm) as a function of Gaussian filter x- and y-width (in pixels), using conventional threshold edge detection.

|  | y-width = 1 | y-width = 2 | y-width = 3 | y-width = 4 |
| --- | --- | --- | --- | --- |
| x-width = 1 |  | 11.17 | 8.52 | 7.28 |
| x-width = 3 | 9.58 | 5.22 | 4.02 | 3.72 |
| x-width = 5 | 8.12 | 4.62 | 3.83 | 3.49 |
| x-width = 7 | 7.44 | 4.50 | 3.78 | 3.42 |
| x-width = 9 | 7.03 | 4.45 | 3.77 | 3.41 |
| x-width = 11 | 6.77 | 4.44 | 3.77 | 3.41 |

Figure 14:
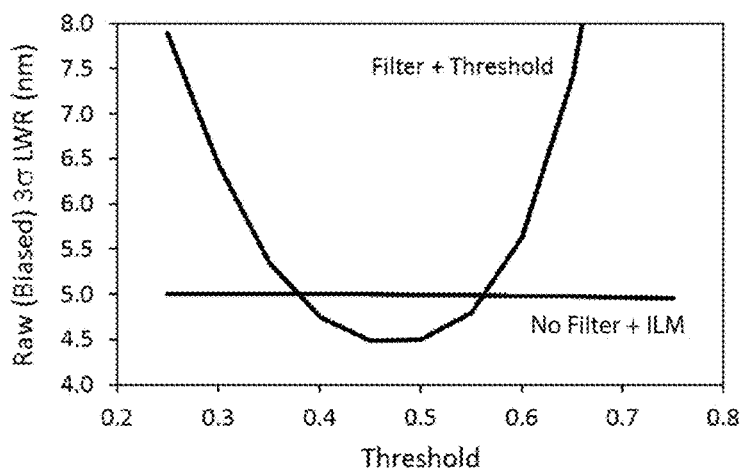
FIG. 14 is a Raw (Biased) linewidth roughness plot vs. threshold settings showing both a prior art result (using a filter with conventional threshold edge detection), and a result using no filter and an inverse linescan model (ILM).

While the arbitrary choice of image filter parameters has a large impact on the measurement of roughness of the pattern structure, the impact of threshold value depends on the specific edge detection method used. For the case of a simple threshold edge detection after image filtering, there is one threshold value that minimizes the 3σ roughness measured, with other values changing the roughness quite dramatically (see FIG. 14). For the case of the ILM, the choice of threshold has almost no impact on the measured LWR (in FIG. 14, the LWR varies from 5.00 nm to 4.95 nm as the threshold is changed from 0.25 to 0.75). Thus, for the conventional prior art method of detecting edges the arbitrary choice of threshold value can cause a large variation in the measured roughness. For the ILM, there are essentially no arbitrary choices that affect the measurement of roughness.

While the disclosed ILM system achieves accurate detection of edges in the presence of high levels of noise, the noise still adds to the measured roughness. For a linescan of a given edge slope, uncertainty in the grayscale values near the line edge translates directly into uncertainty in the edge position. A major difference, though, is that the impact of noise can be measured for the case without filtering. The noise floor of an unfiltered image can be subtracted out from the PSD (power spectral density), producing an unbiased estimate of the PSD (and thus the roughness). For the case of a filtered image, the noise floor is mostly smeared away, so that it cannot be detected, measured, or removed.

Figure 15A:
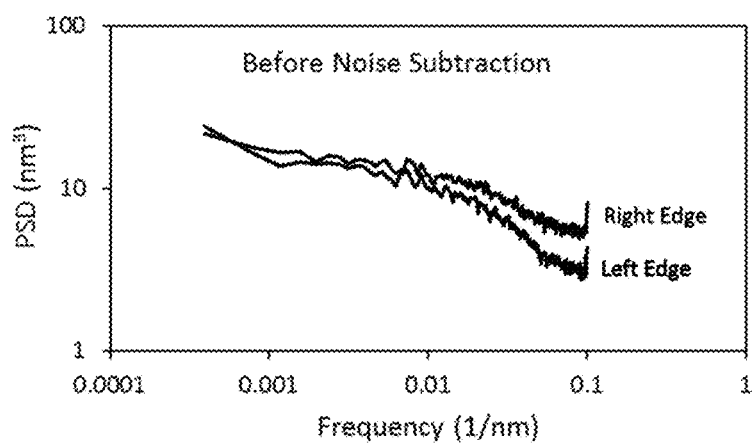
FIG. 15A is a power spectral density (PSD) vs. frequency plot of the right and left edges of a feature shown before noise subtraction.
Figure 15B:
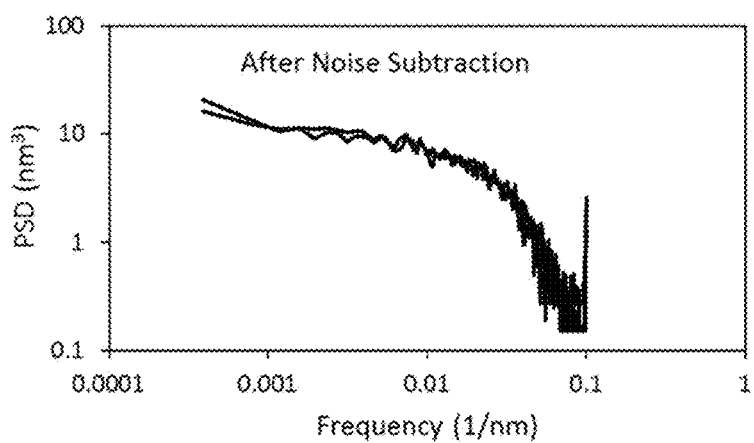
FIG. 15B is a power spectral density (PSD) vs. frequency plot of the right and left edges of a feature shown after noise subtraction.

FIGS. 15A and 15B show LER power spectral densities from many rough features with right and left edges combined separately. More specifically, FIG. 15A shows raw PSDs after edge detection using the disclosed ILM technology, while FIG. 15B shows PSDs after noise subtraction.

Consider the results shown in FIG. 15A, where the line-edge roughness (LER) for the left and right edges of a feature on a pattern structure are compared. The raw PSDs indicate that the two edges behave differently. However, these differences are an artifact of the SEM, caused by a scan-direction asymmetry (such as charging) that makes the right linescan slope lower than the left linescan slope. In fact, there is no difference between right and left edge on the wafer for this sample. By measuring the noise floor for each edge separately, subtracting the noise produces a common left/right LER (FIG. 15B) that is an unbiased estimate of the true PSD.

Once the noise has been subtracted, reliable analysis of the PSD can lead to reliable estimates of the important roughness parameters, such as the zero-frequency PSD(0), the correlation length $\xi$, and the roughness exponent H. The unbiased 3σ roughness can also be obtained. Without removing the noise, extraction of these parameters from the empirical PSD is problematic and prone to systematic errors.

8. Unbiased Measurement of PSD

The biggest impediment to accurate roughness measurement is noise in the CD-SEM image. Among other noise sources, SEM images suffer from shot noise, where the number of electrons detected for a given pixel varies randomly. For the expected Poisson distribution, the variance in the number of electrons detected for a given pixel of the image is equal to the expected number of electrons detected for that pixel. Since the number of detected electrons is proportional to the number of electrons that impinge on the sample location represented by that pixel, relative amount of noise can be reduced by increasing the electron dose that the sample is subjected to. For some types of samples, electron dose can be increased with few consequences. But for other types of samples (such as photoresist), high electron dose leads to sample damage (resist line slimming, for example). Other types of samples, such as biological specimens, can also suffer from electron damage. Thus, to prevent sample damage electron dose is kept as low as possible, where the lowest dose possible is limited by the noise in the resulting image.

FIG. 16 shows portions of three SEM images of nominally the same lithographic features taken at different electron doses. More specifically, FIG. 16 shows portions of SEM images of nominally identical resist features with 2, 8, and 32 frames of integration (respectively, from left to right). Doubling the frames of integration doubles the electron dose per pixel. Since the dose is increased by a factor of 4 in each case, the noise goes down by a factor of 2.

SEM image noise adds to the actual roughness of the patterns on the wafer to produce a measured roughness that is biased higher. Typically, we obtain a biased roughness as given by EQUATION 8A.

$$\sigma_{biased}^2 = \sigma_{unbiased}^2 + \sigma_{noise}^2 \qquad \text{EQUATION 8A}$$

where $\sigma_{biased}$ is the roughness measured directly from the SEM image, $\sigma_{unbiased}$ is the unbiased roughness (that is, the true roughness of the wafer features), and $\sigma_{noise}$ is the random error in detected edge position (or linewidth) due to noise in the SEM imaging and edge detection. EQUATION 8A assumes that the noise is statistically independent of the roughness on the feature being measured. If this is not the case, more complicated noise models can be used, as further described below. Since an unbiased estimate of the feature roughness is desired, the measured roughness can be corrected by subtracting an estimate of the noise term.

Figure 17A:
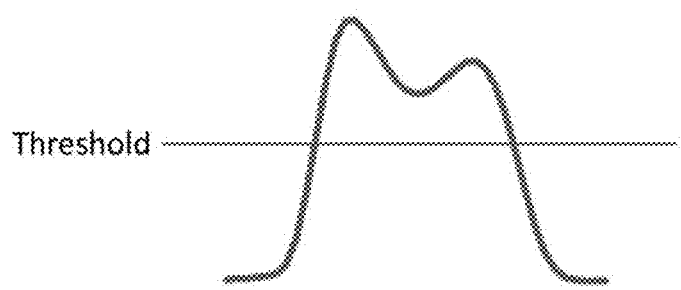
FIG. 17A shows a typical linescan for a line feature on a wafer for a case when there is an extremely large number of electrons so that the pixel noise is negligible.

Pixel noise in the SEM creates edge detection noise depending on the shape of the expected linescan for the feature. For example, FIG. 17A shows a typical linescan (grayscale value versus horizontal position, g(x)) for a line feature on a wafer when there is an extremely large number of electrons so that the pixel noise is negligible. The result is the "expected" linescan, that is, the expectation value of the linescan signal from a statistical perspective. By defining a threshold grayscale level, the edge position can be determined. But noise in the grayscale values results in noise in the detected edge position. For a given grayscale noise $\sigma_{gray}$, the edge position uncertainty $\sigma_{noise}$ will depend on the slope of the linescan at the edge dg/dx. For small levels of noise, $$\sigma_{noise} \sim \frac{\sigma_{gray}}{dg/dx} \qquad (8B)$$

Thus, the level of edge detection noise is a function of the pixel grayscale noise and the slope of the linescan at the feature edge.

Figure 17B:
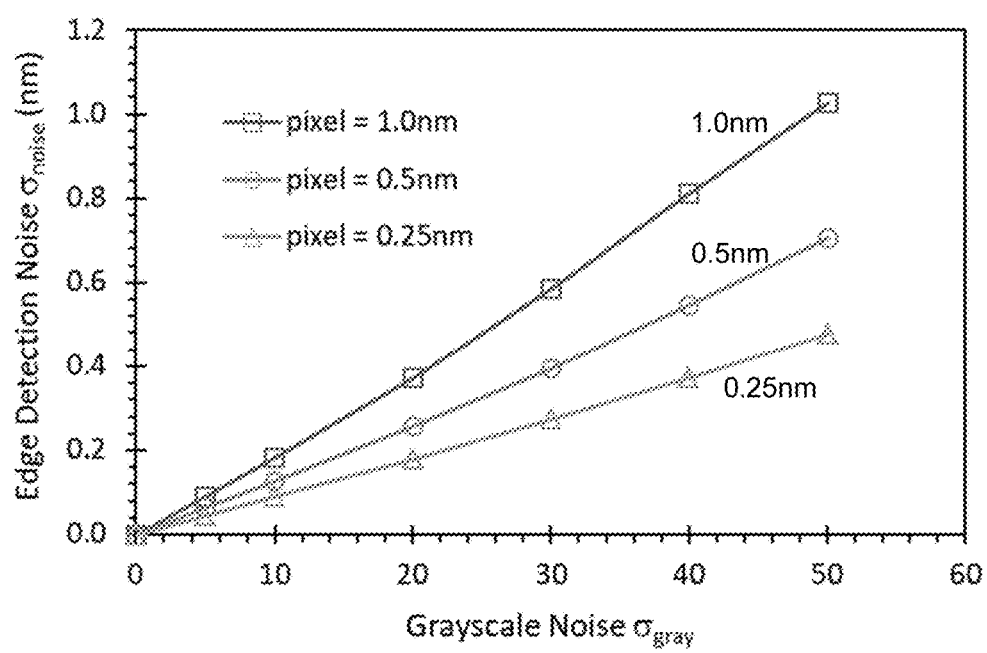
FIG. 17B shows the 1-sigma uncertainty in edge detection position for perfectly smooth features in the presence of grayscale noise, for three different X pixel sizes.

This equation 8B is strictly only valid for small levels of noise and an infinitely small pixel size. To explore the impact of greater amounts of noise and a non-zero pixel size, simulation of SEM images was employed. Perfectly smooth lines and spaces (25 nm width, 50 nm pitch) were used as inputs to the Analytical Linescan Model in order to create synthetic SEM images. Then the resulting grayscale values (which range from 0 to 255) of each pixel were treated as the mean of a normal distribution with a given standard deviation ($\sigma_{gray}$) and a random grayscale number was assigned to each pixel drawn from this normal distribution. These SEM images were then treated as experimental SEM images and measured using an inverse linescan model to detect the edge positions of each feature. The 1-sigma LER measured from these images is the detected edge position uncertainty due to the grayscale pixel noise. FIG. 17B shows the 1-sigma uncertainty in edge detection position for these perfectly smooth features in the presence of grayscale noise. In this graph, the edge detection noise, for three different X pixel sizes, is plotted as a function of grayscale noise for simulated synthetic SEM images (average of 100 images, each with 20 dense lines/space features of width 25 nm and pitch 50 nm). The edge detection used an inverse linescan model and the resulting line-edge roughness of the features was considered to be the edge detection noise. The result is somewhat nonlinear, with higher levels of pixel noise producing ever greater edge detection noise. Further, smaller X pixel sizes produce lower levels of edge detection noise. In fact, the edge detection variance $\sigma_{noise}^2$ is directly proportional to the X pixel size for low levels of grayscale noise.

Pixel noise is not the only source of edge detection noise. During operation the electron beam is scanned from left to right using beam steering electronics. Errors in the beam steering can place the beam at an incorrect position, which produces an edge error. Charging of the sample during electron exposure will deflect the beam to an incorrect position. While some of the charging effects will be systematic, there will also be random or pseudo-random components that will appear as random variation in the detected edge position.

While several approaches for estimating the SEM edge position noise and subtracting it out have been proposed in the prior art, these approaches have not proven successful for today's small feature sizes and high levels of SEM image noise. The problem is the lack of edge detection robustness in the presence of high image noise. More particularly, when noise levels are high, edge detection algorithms often fail to find the edge. The solution to this problem is typically to filter the image, smoothing out the high frequency noise. For example, if a Gaussian 7×3 filter is applied to the image, then for each rectangular region of the image 7 pixels wide and 3 pixels tall, the grayscale values for each pixel are multiplied by a Gaussian weight and then averaged together. The result is assigned to the center pixel of the rectangle. Box (mean) filters and median filters can also be used and produce similar results. This smoothing makes edge detection significantly more robust when image noise is high. FIG. 17C shows an example of using a simple threshold edge detection algorithm with image filtering in the right image and without image filtering in the left image. Without image filtering, the edge detection algorithm is mostly detecting the noise in the image and does not reliably find the edge.

Figure 18:
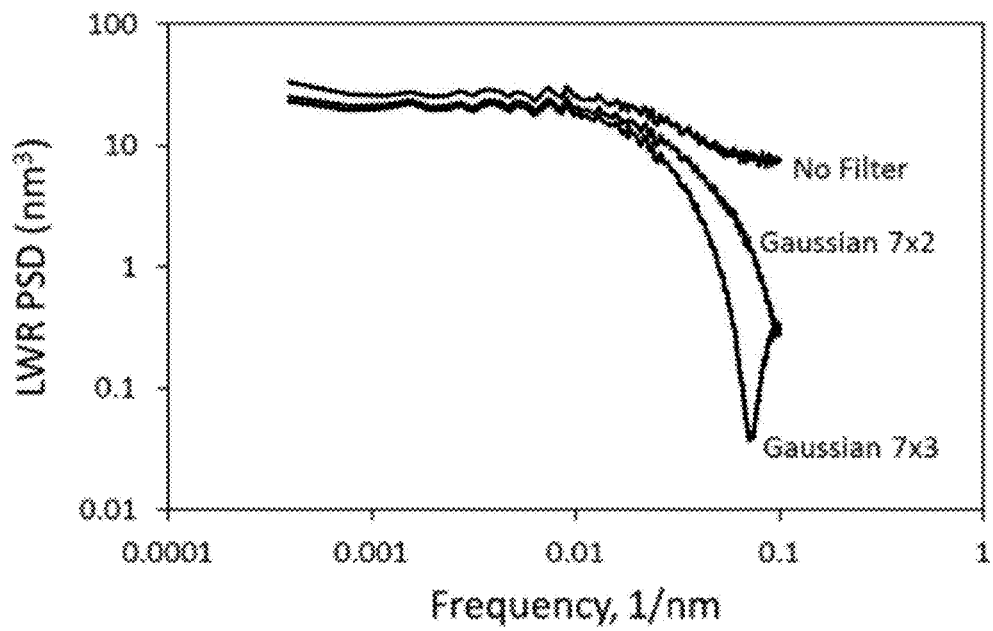
FIG. 18 is a plot of linewidth roughness (LWR) PSD vs. frequency that shows the impact of two different image filters on a collection of 30 images.

The use of image filtering can have a large effect on the resulting PSD and measured roughness. FIG. 18 shows the impact of two different image filters on the PSD obtained from a collection of 30 images, each containing 12 features. All images were measured using an inverse linescan model for edge detection. The power spectral densities were averaged from these 360 rough features with images preprocessed using a 7×2 or 7×3 Gaussian filter, or not filtered at all, as labelled in the drawing. As can be appreciated, the high-frequency region is greatly affected by filtering. But even the low frequency region of the PSD shows a noticeable change when using a smoothing filter. Filtering in the y-direction smoothes out high-frequency roughness. Filtering in the x-direction lowers the slope of the linescan, which can affect measured low-frequency roughness. As will be described next, the use of image filtering makes measurement and subtraction of image noise impossible.

Figure 19:
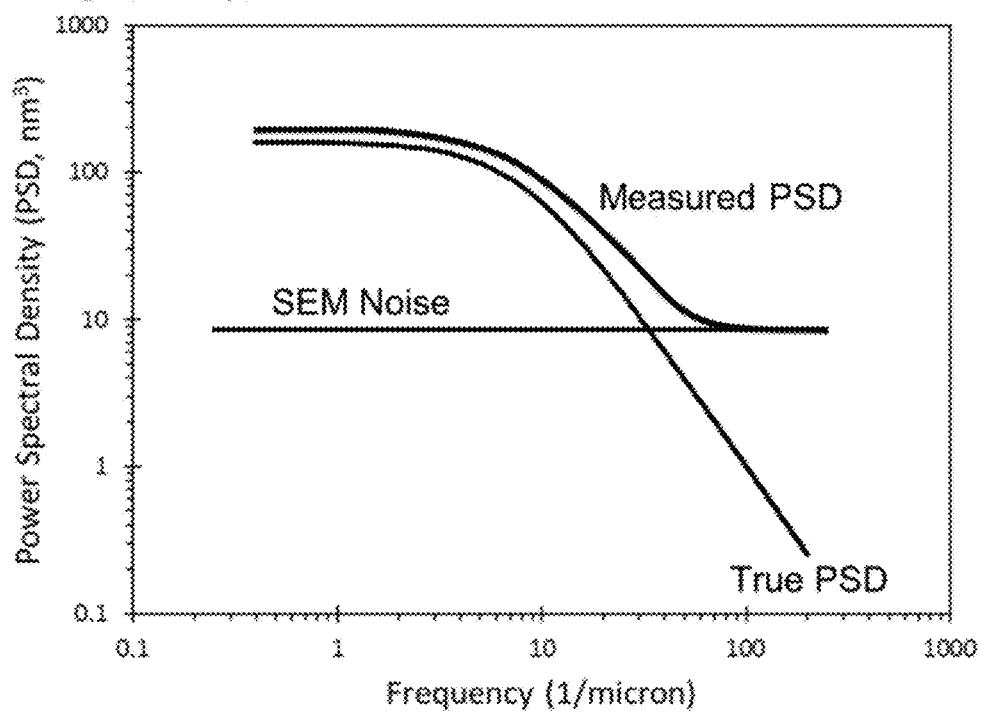
FIG. 19 is a power spectral density plot vs. frequency that shows the noise subtraction process of the disclosed edge detection apparatus and method.

If edge detection without image filtering can be accomplished, noise measurement and subtraction can be achieved by contrasting the PSD behavior of the noise with the PSD behavior of the actual wafer features. We expect resist features (as well as after-etch features) to have a PSD behavior as shown in FIG. 19 as the "True PSD" (and also shown earlier in FIG. 4). Correlations along the length of the feature edge reduce high-frequency roughness so that the roughness becomes very small over very short length scales. SEM image noise, on the other hand, can often be assumed to be white noise, so that the noise PSD is flat over all frequencies. Other models of the SEM image noise are also possible, for example using linescan-to-linescan correlation to describe the noise, as further described below. Thus, at a high enough frequency the measured PSD will be dominated by image noise and not actual feature roughness (the so-called "noise floor"). Given the grid size along the length of the line ($\Delta y$), SEM edge detection white noise affects the PSD according to EQUATION 9 below:

$$\text{PSD}_{biased}(f) = \text{PSD}_{unbiased}(f) + \sigma_{noise}^2 \Delta y \qquad \text{EQUATION 9}$$

Thus, measurement of the high-frequency PSD (in the absence of any image filtering) provides a measurement of the SEM edge detection noise. FIG. 19 illustrates this approach for the case of a white SEM noise model. Clearly, this approach to noise subtraction cannot be used on PSDs coming from images that have been filtered, because such filtering removes the high-frequency noise floor (see FIG. 18).

EQUATION 9 assumes a white noise model, where the noise found in any pixel of the image is independent of the noise found in any other pixel. This may not always be the case. For example, the noise in each pixel may be correlated somewhat with its nearest neighbors, affecting $\sigma_{gray}$ in equation 8B. Alternately, the grayscale slope in equation 8B may be correlated from one row of pixels to the next, possibly caused by the interaction volume of the electrons as shown in FIG. 8. If a correlation model is assumed or measured, a suitable noise expression for the PSD can be used to replace EQUATION 9, as further described below.

FIG. 19 shows one embodiment of the noise subtraction process of the disclosed edge detection apparatus and method. In the disclosed edge detection method, the method first detects the positions of the edges using the ILM without the use of any image filtering (for example, using an inverse linescan method). From these detected edges a biased PSD is obtained, which is the sum of the actual wafer roughness PSD and the SEM noise PSD. Using a model for the SEM image noise (such as a constant white noise PSD), the amount of noise is determined by measuring the noise floor in the high-frequency portion of the measured PSD. The true (unbiased) PSD is obtained by subtracting the noise level from the as-measured (biased) PSD. The key to using the above approach of noise subtraction for obtaining an unbiased PSD (and thus unbiased estimates of the parameters $\sigma_{LWR}(\infty)$, PSD(0), and $\xi$) is to robustly detect edges without the use of image filtering. This can be accomplished using an inverse linescan model. An inverse linescan model was used to generate the no-filter PSD data shown in FIG. 18.

An example method for subtracting white noise will now be described. First, edges are detected from a SEM image without using any image filtering (for example, using an inverse linescan model). The power spectral densities of one or more edges are calculated in the usual way. Since the PSD of a single edge is quite noisy, it is extremely valuable to measure many edges and average the PSDs. Often hundreds or thousands of edges are measured and their PSDs averaged. This averaged PSD is called the biased PSD. From the average biased PSD, the highest frequencies are inspected to determine if a flat noise floor is observed. Such a noise floor is observed whenever the y pixel size is sufficiently smaller than the correlation length of the true roughness. Typically, a y-pixel size that is 20% of the correlation length or smaller is adequate. If a noise floor is observed, the average PSD value in the flat region is calculated. This is the noise floor. This number is then subtracted from the biased PSD at every frequency to produce the unbiased PSD. The biased PSD is our best estimate of the true PSD of the roughness on the wafer.

Other SEM errors can influence the measurement of roughness PSD as well. For example, SEM field distortion can artificially increase the low-frequency PSD for LER and PPR, though it has little impact on LWR. Background intensity variation in the SEM can also cause an increase in the measured low-frequency PSD, including LWR as well as LER and PPR. If these variations can be measured, they can potentially be subtracted out, producing the best possible unbiased estimate of the PSD and its parameters. By averaging the results of many SEM images where the only common aspect of the measurements is the SEM used, determination of SEM image distortion and background intensity variation can be made.

9. Sensitivity to Metrology Tool Settings

Not all noise in measured PSDs is white noise. White noise occurs when the measurement noise of the edge position from each linescan is completely independent of all other linescans (and in particular, its nearest neighbors). White noise occurs in the absence of correlations that connect the errors in one linescan to the errors in the neighboring linescans. Any small correlations in edge errors along the length of the line would cause "pink noise", a noise signature that is not perfectly flat over the entire frequency region.

The settings of the SEM metrology tool can impact the measured roughness of a feature in a pattern structure. These settings include the magnification and pixel size of SEM 701. These two parameters can be changed independently by changing the number of pixels in the image (from 512×512 to 2048×2048, for example). Additionally, the number of frames of integration (the electron dose) when capturing an SEM image can be adjusted. To study the impact of this setting, the number of frames of integration can be varied from 2 to 32, representing a 16× variation in electron dose, for example.

Figure 20:
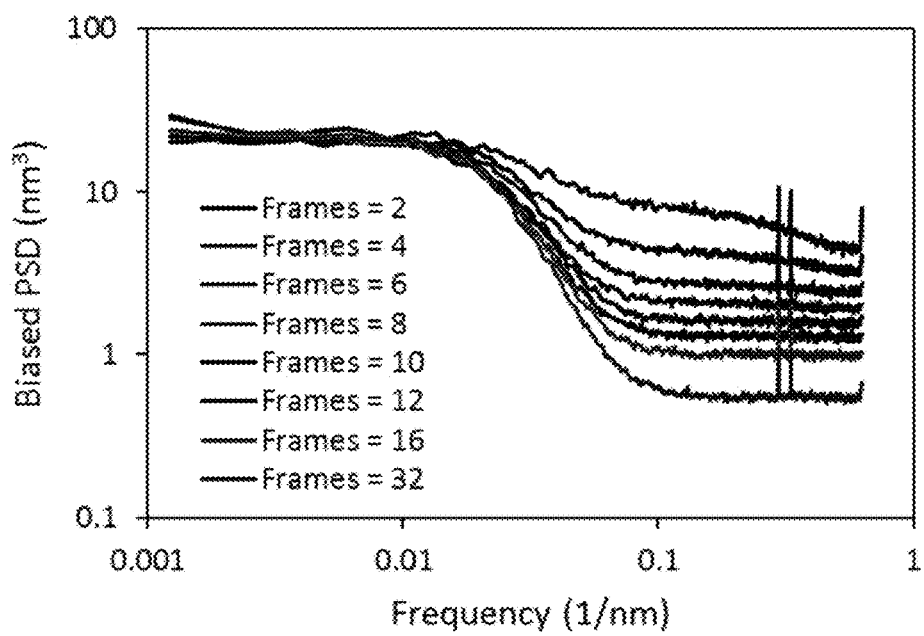
FIG. 20 shows PSDs of a particular resist feature type on a given wafer, measured with different frames of integration in the SEM.

Total electron dose is directly proportional to the number of frames of integration. Thus, shot noise and its impact on edge detection noise is expected to be proportional to the square root of the number of frames of integration. FIG. 20 shows PSDs of a particular resist feature type on a given wafer, measured with different numbers of frames of integration. In this case, the PSDs correspond to 18 nm resist lines and spaces where only the number of frames of integration was varied. SEM conditions used were 500 eV, 49 images per condition, 21 features per image, pixel size=0.8 nm square, and image size=1024×1024 pixels. The cases of 8 or more frames of integration produce PSDs that exhibit a fairly flat high-frequency noise region. For 2 and 4 frames of integration (the upper-most two graphed lines in the figure), the noise region is noticeably sloped. Thus, the assumption of white SEM noise is only approximately true, and becomes a more accurate assumption as the number of frames of integration increases and noise level decreases. This observation has been borne out in other circumstances: High noise cases are more likely to exhibit non-flat noise floors.

Figure 21:
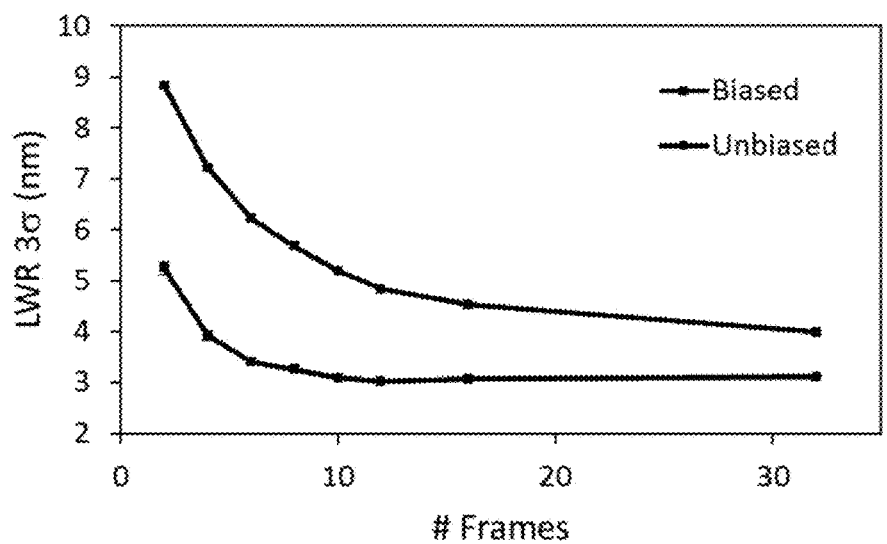
FIG. 21 shows the biased and unbiased values of the 36 linewidth roughness (LWR) measured as a function of the number of frames of integration in the SEM.

FIG. 21 shows the biased values (upper graphed line) and unbiased values (lower graphed line) of the 3σ linewidth roughness measured as a function of the number of frames of integration. All conditions were the same as described in FIG. 20, and error bars represent 95% confidence interval estimates. The biased roughness varies from 8.83 nm at two frames of integration to 5.68 nm at 8 frames and 3.98 nm at 32 frames. The unbiased roughness, on the other hand, is fairly stable after 6 frames of integration, varying from 5.25 nm at two frames of integration to 3.25 nm at 8 frames and 3.11 nm at 32 frames. While the biased roughness is 43% higher at 8 frames compared to 32, the unbiased roughness is only 4% higher at 8 frames compared to 32. Since the assumption of white SEM noise is not very accurate at 2 and 4 frames of integration, the noise subtraction of the unbiased measurement using a white noise model is not completely successful at these very low frames of integration. A correlated noise model can produce better noise subtraction especially for the low frames of integration, as is more fully described below. While the results shown are for LWR, similar results are obtained for the measurement of line edge roughness (LER) and pattern placement roughness (PPR).

One possible cause of correlations in edge noise would be correlations in the pixel noise. To test this possibility, isolated edges were measured in the CD-SEM. The edge allows the SEM to perform its imaging functions in a typical way, but at a distance left or right from the edge the field is flat and featureless. In this region the only variation in pixel grayscale values comes from image noise. The correlation coefficient between neighboring pixels can then be calculated. Performing these calculations, the average correlation between neighboring pixels in the x-direction was 0.12, but the average correlation in the y-direction was only 0.01, essentially zero. These correlations coefficients were determined for edges measured at 2 to 32 frames of integration. There was little variation in the pixel-to-pixel correlation as a function of the number of frames of integration. Thus, correlated pixel noise is not responsible for the pink noise observed at low frames of integration. However, it is possible that the linescan slope in equation 8B is responsible for the noise correlations.

A possible cause of noise correlations in the linescan slope comes from the interaction of the beam with the sample. Electrons striking the sample undergo a number of processes that depend on the energy of the electron and the material properties of the sample. Electrons scatter off the atoms of the sample material, release energy, change direction, and often generate a cascade of secondary electrons by ionizing the sample atoms. Occasionally electrons ricochet backwards off the atom nucleus and exit out of the sample (called backscatter electrons). Some of the lower energy secondary electrons can also escape out of the sample (frequently through the edges of a feature, see FIGS. 8A and 8B). The way in which a SEM forms an image is by detecting the number of secondary electrons and/or backscatter electrons that escape the sample for each beam position.

When forming an image using an SEM, a small spot of electrons dwells at a specific point on the sample (i.e., a pixel) while the number of escaping secondary electrons is counted by the secondary electron detector. When the spot is a long way from a feature edge, as in FIG. 8A, the number of detected secondary electrons 805 is small (and the pixel is dark). When the spot is near a feature edge, as in FIG. 8B, secondary electrons 805 from the interaction volume readily escape from the feature edge producing a bright pixel.

The interaction volume of the electrons can be one to a few tens of nanometers in diameter, depending on the beam voltage and the sample material properties. This interaction volume means that electrons impinging on one spot on the sample are influenced by the sample shape over a range determined by the interaction volume. Thus, the slope of the linescan at one row of pixels will not be independent of the slope of the linescan at neighboring pixels whenever the interaction volume radius is greater than the y pixel size.

This dependency could be the cause of correlations in the noise, with a noise correlation length affected by the electron beam interaction volume.

10. Removing Pink Noise from a Power Spectral Density

Figure 25:
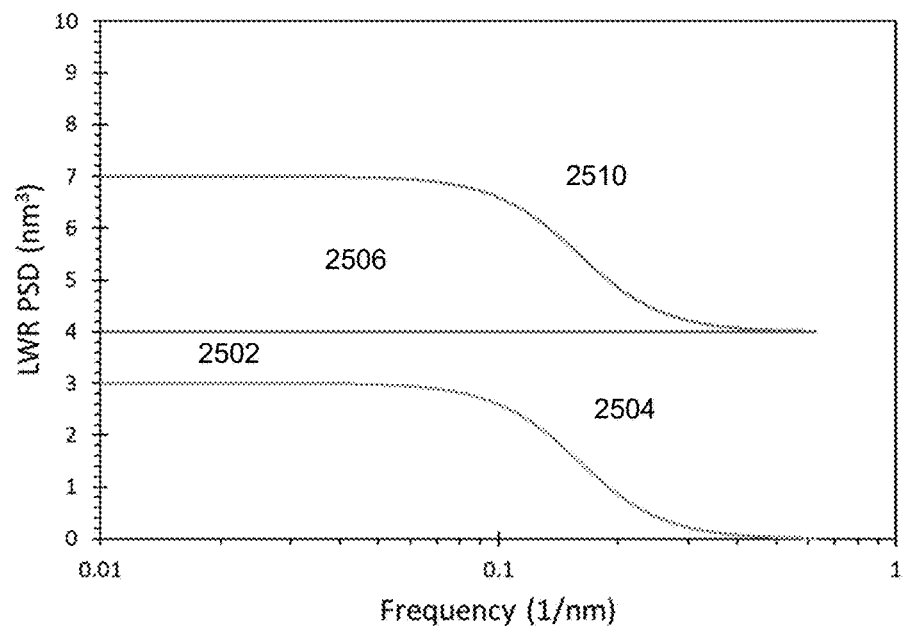
FIG. 25 shows a pink noise model as described in some embodiments.

The above discussion of white noise provides a basic method of removing white noise from a PSD contaminated with it. The model for white noise is a flat (constant) PSD of the noise, which adds to the PSD of the feature roughness. For pink noise, a more complicated model is required. When determining a reasonable model for pink noise, it is instructive to recognize the role of correlations in the noise signature. Like roughness itself, correlations in noise reduce the noise at high frequencies (those higher than the frequency corresponding to the correlation length of the noise). Thus, as depicted in FIG. 25, a PSD model for pink noise will be similar to a PSD model for the roughness itself: a flat (white) value 2502 at low frequencies, transitioning to fractal (sloping downward) region 2504 at length scales below the correlation length. This correlated noise model can then be added to a white noise model 2506 to create the final pink noise model 2510.

A useful form for a pink noise model is given in Equation 10 below:

$$PSD_{noise}(f) = \frac{PSD_{low} - PSD_{high}}{1 + |2\pi f \xi_{noise}|^B} + PSD_{high} \quad (10)$$

where $PSD_{low}$ is the low-frequency portion of the pink noise, $\xi_{noise}$ is the correlation length of the noise, B is a power that defines how fast the noise transitions from the low-frequency region to the high-frequency region, and $PSD_{high}$ is the noise level in the high-frequency region. For this model, Low Frequencies: $PSD_{noise}(f) \approx PSD_{low}$ High Frequencies: $PSD_{noise}(f) \approx PSD_{high}$ (11)

The transition from the low-frequency region to the high-frequency region occurs at a frequency of $1/(2\pi\xi_{noise})$. The power B is not particularly important, and can easily be fixed at a reasonable value, such as somewhere in the range from 2-6. Here, a value of 4 will be used. Thus, the key parameters of the pink noise model are $PSD_{low}$, $\xi_{noise}$, and $PSD_{high}$.

Figure 26:
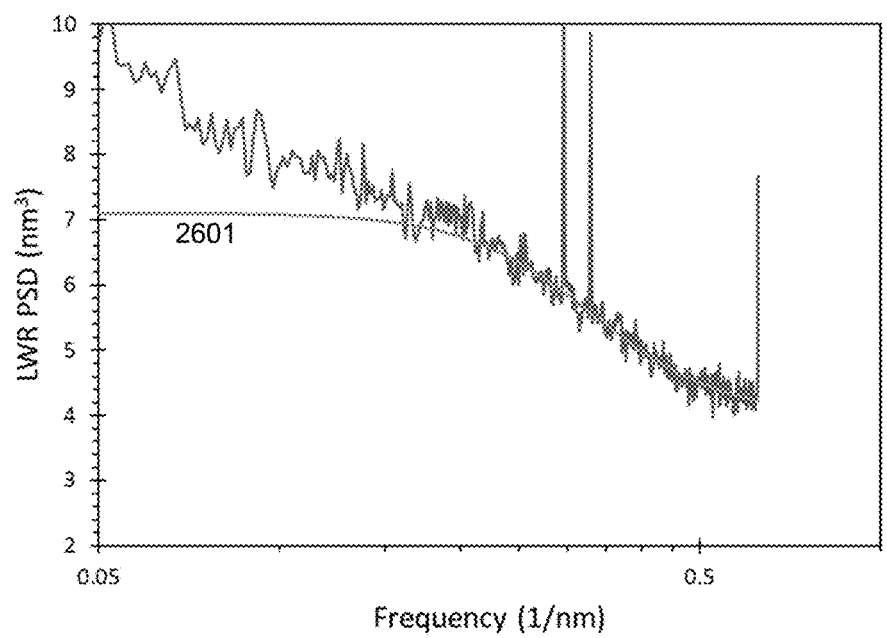
FIG. 26 shows the mid to high frequency region of one of the PSD datasets from FIG. 20, for the case of 2 frames of integration, and shows this region well fit by a pink noise model of FIG. 25.

Comparisons of this model to observations have shown that it fits data quite well under a variety of conditions. Shown in FIG. 26 is one of the PSD data sets from FIG. 20, for the case of 2 frames of integration (here showing only the mid to high frequency region). The high frequency region can be well fit by the pink noise model using $PSD_{low}$=4.0 nm³, $PSD_{high}$=7.1 nm³, and $\xi_{noise}$=0.48 nm, as shown by the curve 2601. The small correlation length means that the noise in edge detection at a given pixel row is influenced almost exclusively by its two neighboring pixel rows, the one just above and the one just below.

The difference between using a white noise model and a pink noise model can be seen in FIGS. 27A and 27B and Table 3 for the case of the 2 frames of integration data from FIG. 20. FIG. 27A shows biased PSD data and only white noise subtraction to generate the unbiased PSD data, and FIG. 27B shows biased PSD data and pink noise subtraction to generate the unbiased PSD data. The resulting unbiased PSD (after noise subtraction) follows the expected shape only for the case of pink noise subtraction. The difference in the extracted roughness parameters is quite significant when comparing white noise removal to pink noise removal (see Table 3). For white noise removal, the unbiased PSD exhibits a shape quite different from the PSD model, making model fitting and parameter extraction potentially unreliable.

TABLE 3

|  | White Noise Removal | Pink Noise Removal |
|---|---|---|
| 3σ LWR (nm) | 5.18 ± 0.07 | 3.73 ± 0.12 |
| PSD(0) (nm³) | 16.27 ± 0.85 | 15.19 ± 0.35 |
| Correlation Length (nm) | 3.19 ± 0.23 | 5.73 ± 0.17 |
| Roughness Exponent | 0.5 | 0.83 ± 0.06 |

Figure 28:
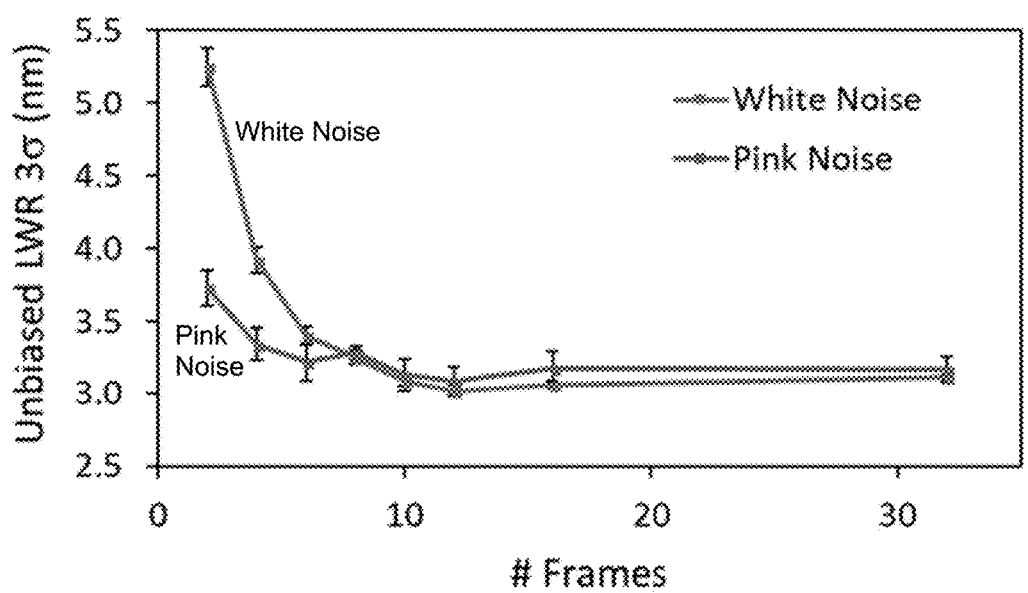
FIG. 28 shows, for a representative example, the estimated unbiased LWR 3σ estimates as a function of the number of frames of integration for both pink noise and white noise removal.

The data from FIGS. 20 and 21 can be used to explore the efficacy of the pink noise removal process. FIG. 28 shows the estimated unbiased LWR 3σ estimates as a function of the number of frames of integration for both pink noise and white noise removal. Ideally, every measurement would produce the same unbiased LWR value (i.e., a flat line when plotted as a function of the number of frames) to within measurement uncertainty since the true roughness on the wafer is a constant (i.e., not dependent on metrology settings such as the number of frames of integration). As can be seen in FIG. 28, pink noise subtraction does a better job of providing an unbiased LWR estimate over a wider range of frames of integration. In particular, the 2, 4, and 6 frames data produce much better unbiased roughness estimates using the pink noise model. For example, for the case of 4 frames of integration compared to 32 frames of integration, white noise subtraction produces an estimate that is 26% too high, whereas pink noise subtraction produces an estimate that is only 5% too high (within measurement uncertainty for this experiment).

Figure 29:
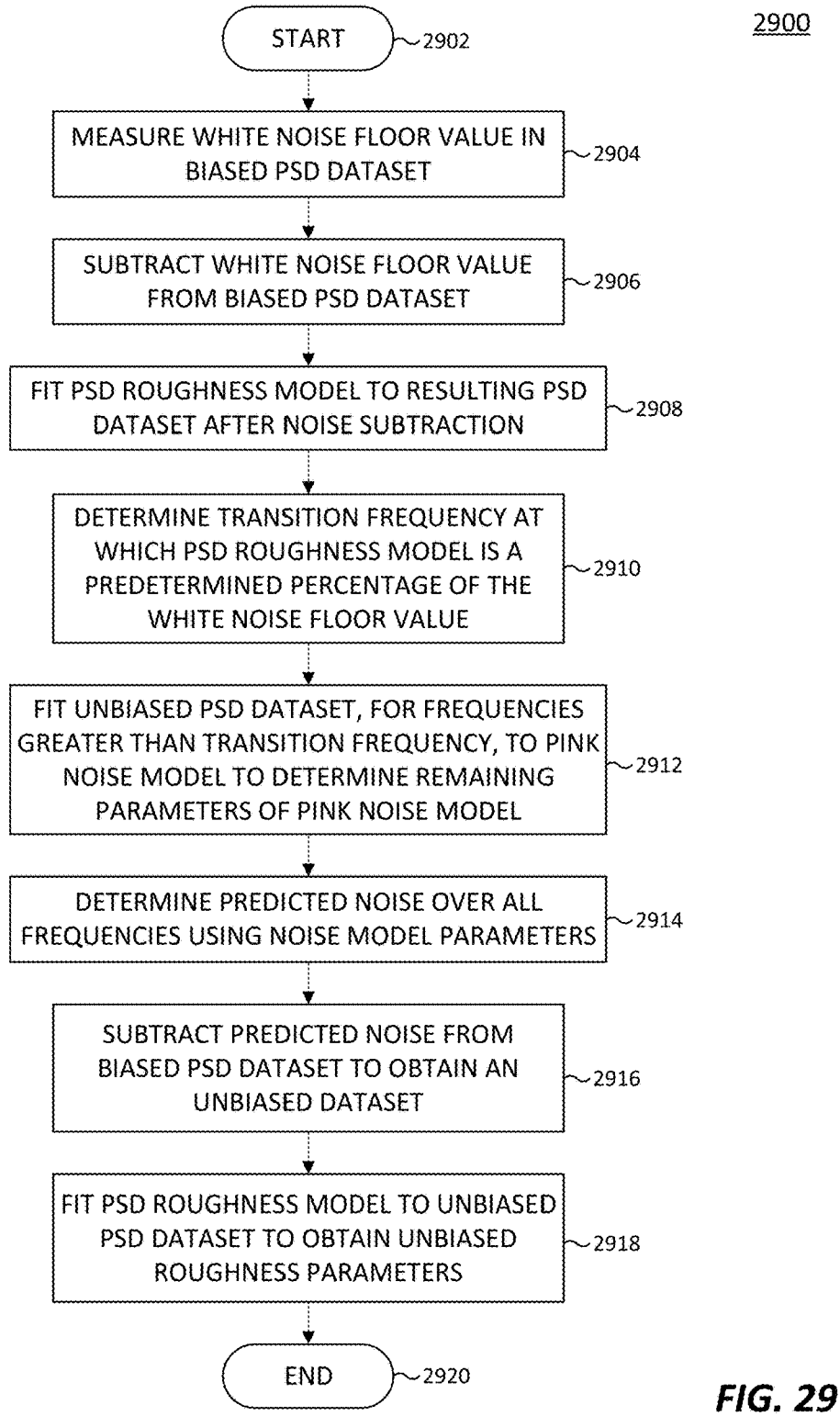
FIG. 29 is a flowchart that depicts a representative process flow to model noise in a biased PSD dataset as pink noise, and to remove the noise from the biased PSD dataset and obtain unbiased roughness parameters for a feature.

Referring now to FIG. 29, an example method 2900 for subtracting pink noise from a biased PSD dataset will now be described. The method 2900 begins at start block 2902. First, white noise is assumed and, per block 2904, a white noise floor value of the biased PSD dataset is measured. At block 2906, the white noise floor value is subtracted from the biased PSD dataset. In some embodiments, the procedure described above can be used to measure and subtract out the white noise floor value. This provides a measurement of $PSD_{high}$ from equation (10). Next, at block 2908, the PSD model of the roughness is fit to the resulting PSD dataset after white noise subtraction (for example, as seen in FIG. 27A). Since the PSD of the roughness falls off as a power of frequency for high frequencies, there comes a point where the PSD model of the roughness (i.e., the PSD roughness model) becomes small compared the white noise level (for example, ten times smaller). We can define the transition frequency as the value of the frequency where the PSD roughness model is some multiple (for example, 10) times smaller than the measured white noise. In other words, we can define the transition frequency as the value of the frequency where the PSD roughness model is a predetermined percentage of the measured white noise (e.g., 10% of the measured white noise). For all frequencies larger than this transition frequency, the biased PSD dataset is essentially noise rather than roughness. To model this noise, the biased PSD dataset for all frequencies greater than the transition frequency is then fitted to the pink noise model, such as equation (10), per block 2912. For example, a method of minimizing the least squares difference between model and data can be used. This will provide best fit values for the remaining two noise parameters in the pink noise model (i.e., the $PSD_{low}$ and $\xi_{noise}$) as well as another measurement of $PSD_{high}$. These three noise model parameters can be used, per block 2914, to determine the predicted noise over all frequencies. Then, per block 2916, the predicted noise is subtracted from the biased (measured) PSD data to obtain the unbiased PSD dataset (for example, as seen in FIG. 27B). Lastly, at block 2918, the unbiased PSD dataset is then fitted to a PSD roughness model to obtain unbiased roughness parameters. The method 2900 finishes at end block 2920.

In another example method for subtracting pink noise from a biased PSD dataset, a pink noise model, such as that represented by equation (10), could be added to a PSD model of the roughness to produce a single equation for roughness and noise. For example, the following equation 12 could be used to model the PSD of the roughness (without noise):

$$PSD_{roughness}(f) = \frac{PSD_{roughness}(0)}{1 + |2\pi f \xi_{roughness}|^{2H+1}} \quad (12)$$

Here three parameters are used to define the roughness ($PSD_{roughness}(0)$, $\xi_{roughness}$, and H). Other PSD expressions are possible, including discrete PSD expressions or expressions that include aliasing, spectral leakage, and other effects. Adding equations (10) and (12) produces one expression with six unknowns (if B can be fixed) or seven unknowns (if B is allowed to vary) that describes the as-measured (biased) PSD. Fitting this combined equation to the biased PSD in one step would allow all six or seven unknown parameters to be determined as best-fit parameters. The resulting roughness parameters ($PSD_{roughness}(0)$, $\xi_{roughness}$, and H) found in this way would represent unbiased PSD parameters. The unbiased PSD can be obtained by subtracting the evaluated noise model from the biased PSD.

Figure 30:
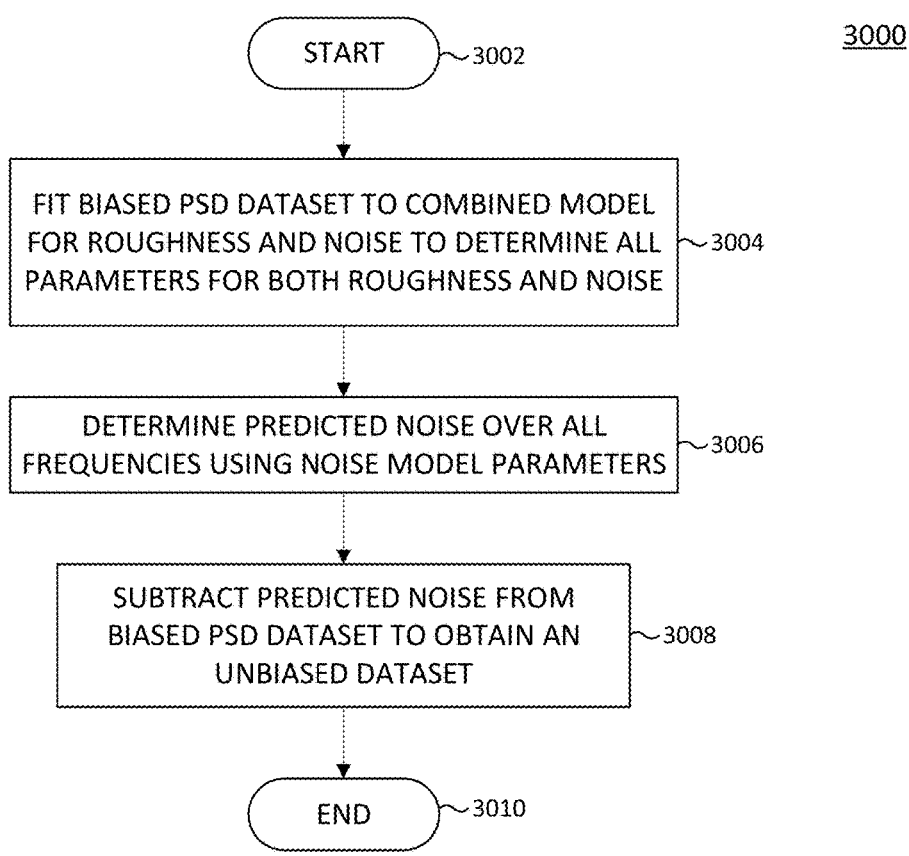
FIG. 30 is a flowchart that depicts another representative process flow to model noise in a biased PSD dataset as pink noise, and to remove the noise from the biased PSD dataset and obtain unbiased roughness parameters for a feature.

Referring now to FIG. 30, an example method 3000 for subtracting pink noise from a biased PSD dataset utilizes such a combined model representing both roughness and noise. The method 3000 begins at start block 3002. At block 3004, the combined model for roughness and noise is fitted to the biased PSD dataset to determine all parameters for both roughness and noise. At block 3006, the noise model parameters are used to determine the predicted noise over all frequencies. At block 3008, the predicted noise is subtracted from the biased PSD dataset to obtain an unbiased PSD dataset. The method 3000 finishes at end block 3010.

Additionally, the two approaches represented by methods 2900 and 3000 above can be combined. For example, the first multi-step fitting method 2900 can be used to obtain a first estimate of noise and unbiased PSD parameters. These six or seven parameters can then be used as the starting point for an iterative fitting of the combined roughness+noise model in one step, as described in the second method 3000. In some embodiments, an iterative non-linear least-squares fitting method can be used to fit the combined roughness+noise model to the biased PSD dataset. The combination of multi-step fitting followed by single-step fitting will often represent the best trade-off between accuracy and robustness of the model fitting procedure.

The pink PSD model can also be combined with equation 8A to obtain the unbiased roughness variance and standard deviation. Integrating the pink noise PSD model over all frequencies gives a measurement of the noise variance, $\sigma_{noise}^2$. Subtracting the noise variance from the biased variance gives the unbiased variance. Such an unbiased variance is an example of an unbiased roughness measure. Other examples of an unbiased roughness measure include roughness parameters corresponding to the unbiased PSD dataset.

Figure 31:
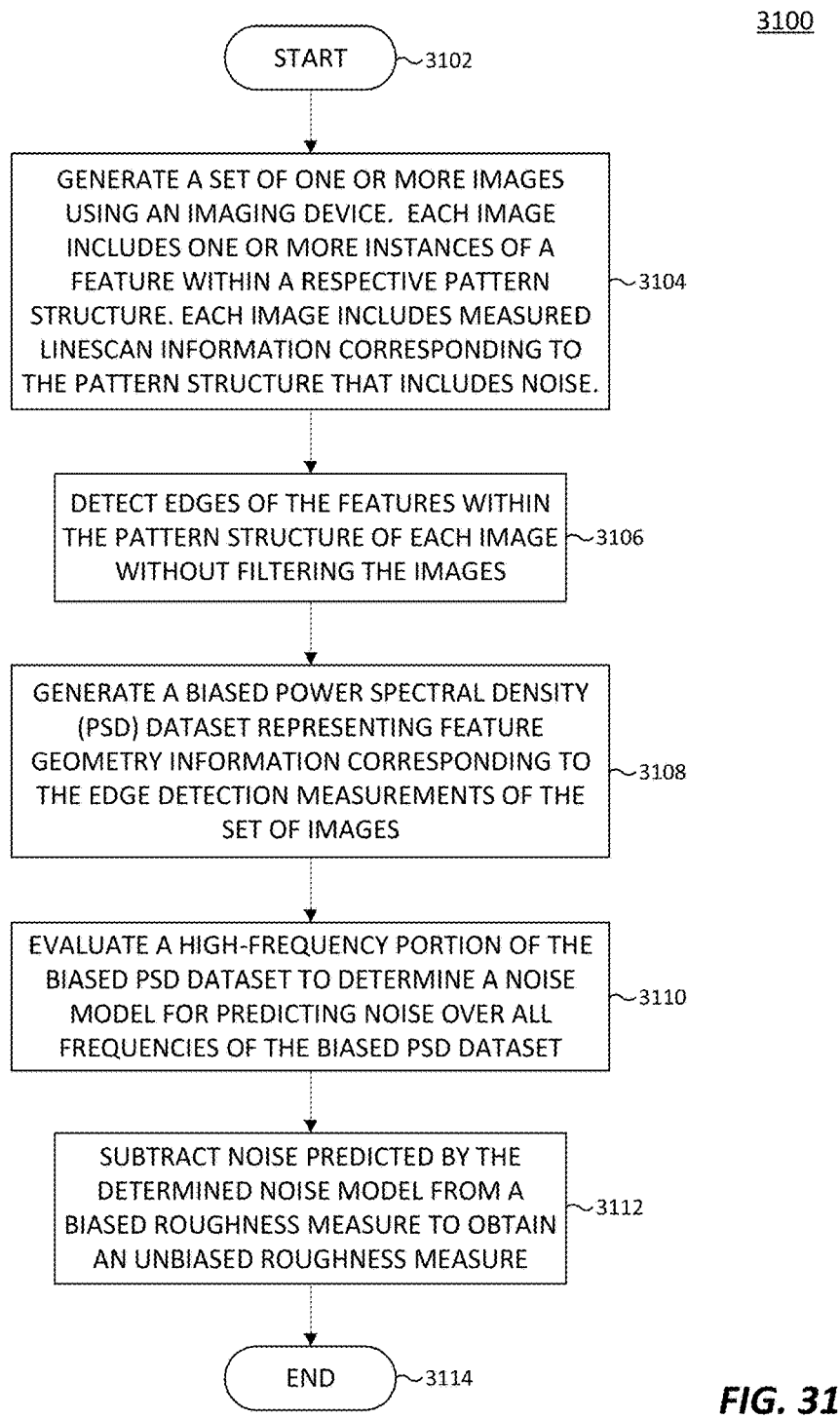
FIG. 31 is a flowchart that depicts a representative process flow to model and remove noise from a biased PSD dataset and obtain an unbiased roughness measure of a feature.

Referring now to FIG. 31, an example method 3100 for unbiased roughness measurement is depicted. The method 3100 begins at start block 3102. At block 3104, a set of one or more images is generated using an imaging device. Each image of the set includes one or more instances of a feature within a respective pattern structure, and each image includes measured linescan information corresponding to the pattern structure that includes noise. In some embodiments a single pattern structure containing a single feature may be imaged. In other embodiments each pattern structure can include multiple features, and multiple such pattern structures may be imaged. At block 3106, the feature edges within the pattern structure of each image are detected without filtering the images (that is, without applying a filter to the image which would appreciably affect the shape of the resulting PSD). In some embodiments, an inverse linescan model (ILM) can be used to detect the features edges. At block 3108, a biased PSD dataset is generated representing feature geometry information corresponding to the edge detection measurements of the set of images. At block 3110, the high-frequency portion of the biased PSD dataset is evaluated to determine a noise model for predicting noise over all frequencies of the biased PSD dataset, and at block 3112, the noise predicted by the determined noise model is subtracted from a biased roughness measure to obtain an unbiased roughness measure. In some embodiments, the biased roughness measure can be a biased PSD dataset. In some embodiments, the unbiased roughness measure can be an unbiased PSD dataset. In some embodiments, the unbiased roughness measure can be parameters corresponding to an unbiased PSD dataset. In some embodiments, the unbiased roughness measure can be an unbiased variance or unbiased standard deviation as described above. The method 3100 finishes at end block 3114.

The flowcharts of FIG. 29, FIG. 30, and FIG. 31 includes the steps that can be performed using the system 700 depicted in FIG. 7, including certain steps that can be carried out by the SEM 701 and certain other steps that can be carried out by the information handling system (IHS) 750 and its included processor 755 and storage 760, both as described in detail herein. Instructions can be stored in storage 760 that, when executed by the processor, cause the processor to perform the methods disclosed herein and described by the flowcharts of FIG. 29, FIG. 30, and FIG. 31, in analogous fashion as other instructions stored in storage 760 that implement the inverse linescan model metrology tool 765 described herein.

11. Influence of Pixel Size and Magnification

Figure 22A:
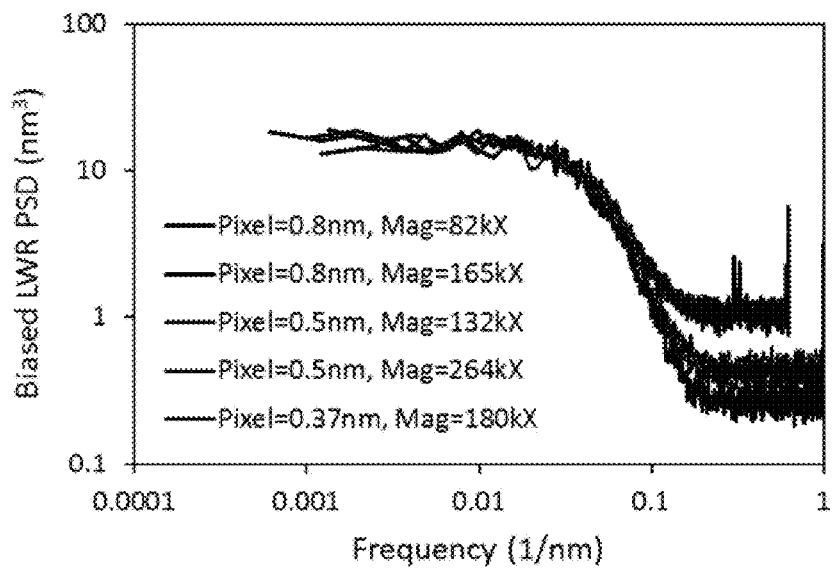
FIG. 22A shows biased linewidth roughness (LWR) power spectral densities (PSDs) as a function of different pixel sizes and magnifications employed by the SEM.
Figure 22B:
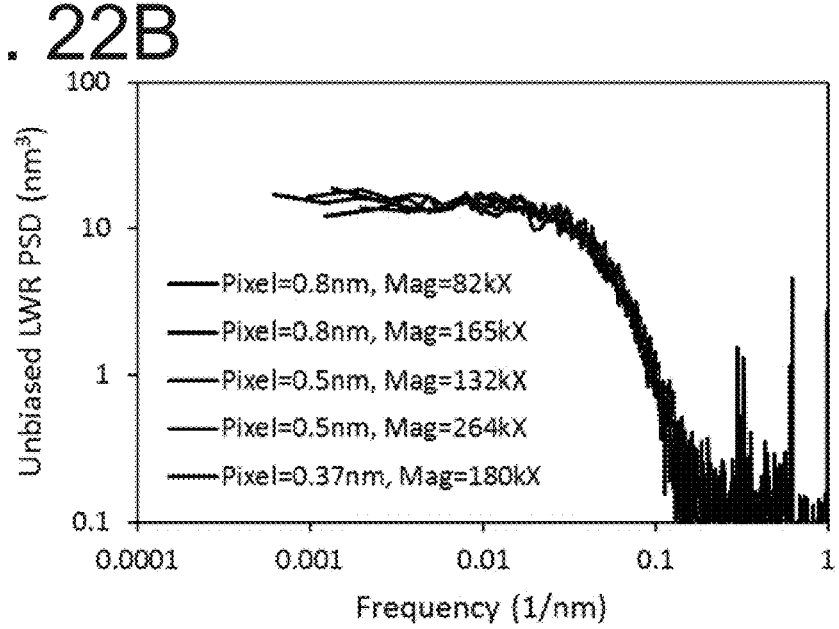
FIG. 22B shows unbiased linewidth roughness (LWR) power spectral densities (PSDs) as a function of different pixel sizes and magnifications employed by the SEM.

With respect to the pixel size and magnification employed by SEM 701, FIGS. 22A and 22B show the biased and unbiased power spectral densities (PSDs), respectively, for a pattern of 16 nm lines and spaces for different magnifications and pixel sizes, assuming a white noise model. For a given number of frames of integration, changing the pixel size changes the electron dose per unit wafer area and the noise in the SEM image. Table 3 shows the measured 36 linewidth roughness (LWR), as well as the other PSD parameters, for these different pixel size and magnification conditions. Under this range of conditions, the biased LWR varied by 0.63 nm (14%), while the unbiased LWR varied by only 0.07 nm (2%). The unbiased LWR is essentially unaffected by these metrology tool settings. Similar results are obtained for the measurement of LER and PPR.

FIGS. 22A and 22B show power spectral densities as a function of pixel size and magnification. More particularly, FIG. 22A shows the biased LWR PSD and FIG. 22B shows the unbiased LWR PSD after noise has been measured and subtracted off. The SEM conditions for these results used a landing energy of 500 eV, 3 images per condition, and 16 nm resist lines and spaces.

TABLE 4 below shows the measured PSD parameters for the PSDs shown in FIGS. 22A and 22B.

TABLE 4

Biased and unbiased 3σ LWR (nm) measurements as a function of pixel size and magnification.

|  | Pixel 0.8 nm 82 kX | Pixel 0.8 nm 164 kX | Pixel 0.5 nm 130 kX | Pixel 0.5 nm 264 kX | Pixel 0.37 nm 180 kX |
|---|---|---|---|---|---|
| Biased LWR (3-sigma, nm) | 5.10 | 4.99 | 4.67 | 4.61 | 4.47 |
| Unbiased LWR (3-sigma, nm) | 3.66 | 3.65 | 3.70 | 3.67 | 3.63 |
| Unbiased LWR PSD(0) (nm$^3$) | 15.95 | 16.18 | 17.2 | 16.25 | 16.35 |
| LWR Correlation Length (nm) | 5.08 | 5.05 | 5.31 | 5.11 | 5.38 |

It has been found that the difference between biased and unbiased LWR is not constant, but varies with metrology tool settings, feature size, and process. Likewise, the ratio between biased and unbiased LWR varies with metrology tool settings, feature size, and process. TABLE 5 below shows the difference and ratio of biased to unbiased LWR for a variety of conditions. For these conditions, the ratio of biased to unbiased LWR varies from 1.09 to 1.66. The difference between biased and unbiased LWR varies from 0.32 nm to 2.19 nm in this particular example.

TABLE 5

The relationship between biased and unbiased LWR for a variety of processes.

| Process | 3σ LWR: Biased/Unbiased | 3σ LWR (nm): Biased − Unbiased |
|---|---|---|
| 193i litho, 84 nm pitch, 500 V, 512 rect pixels | 1.20 | 0.76 |
| 193i etch, 84 nm pitch, 800 V, 512 rect pixels | 1.14 | 0.43 |
| EUV litho, 32 nm pitch, 500 V, 2048 0.8 nm pixels | 1.39 | 1.44 |
| EUV litho, 32 nm pitch, 500 V, 1024 0.8 nm pixels | 1.37 | 1.34 |
| EUV litho, 32 nm pitch, 500 V, 2048 0.5 nm pixels | 1.26 | 0.97 |
| EUV litho, 32 nm pitch, 500 V, 1024 0.5 nm pixels | 1.26 | 0.94 |
| EUV litho, 32 nm pitch, 500 V, 1024 0.37 nm pixels | 1.23 | 0.84 |
| EUV litho, 36 nm pitch, 500 V, 1024 0.8 nm pixels | 1.52 | 1.86 |
| EUV litho, 32 nm pitch, 500 V, 1024 rect pixels | 1.66 | 2.19 |
| EUV etch, 32 nm pitch, 800 V, 1024 rect pixels | 1.09 | 0.32 |

12. Edge Detection Embodiments

FIG. 23 is a flowchart that depicts a representative overall process flow that the disclosed SEM edge detection system employs to detect edges of a pattern structure. For discussion purposes, the process described in the flowchart of FIG. 23 is applied to sample 2400 of FIG. 24A. Sample 2400 is a pattern structure that may also be referred to as pattern structure 2400. The flowchart of FIG. 23 includes the steps carried out by inverse linescan model metrology tool 765 to determine the edges of the pattern structure.

Process flow commences at start block 2300 of FIG. 23. As seen in FIG. 7, an information handling system (IHS) 750 is coupled to SEM 701 to receive SEM linescan image information from SEM 701. IHS 750 includes a processor 755 and storage 760 coupled thereto. Storage 760 may include volatile system memory and non-volatile permanent memory such as hard drives, solid state storage devices (SSDs) and the like that permanently store applications and other information. Storage 760 stores the inverse linescan model (ILM) metrology tool 765 disclosed herein and described by the flowchart of FIG. 23. SEM 701 includes a controller (not shown) that IHS 760 instructs to perform image acquisition on pattern structure 800 and that provides linescan information from SEM 701 to IHS 750.

As per block 2305, SEM 701 sends an SEM image of pattern structure 800 to IHS 750, and in response, IHS 750 loads this SEM image into system memory within storage 760. IHS 750 preprocesses the pattern structure image from the SEM 701, as per block 2310. For example, this preprocessing of the loaded SEM image may include adjusting grayscale values and subtracting out background tilts of intensity levels. Optionally, as per block 2315, IHS 750 may perform filtering of the loaded image, although this is generally not preferred.

Figure 24A:
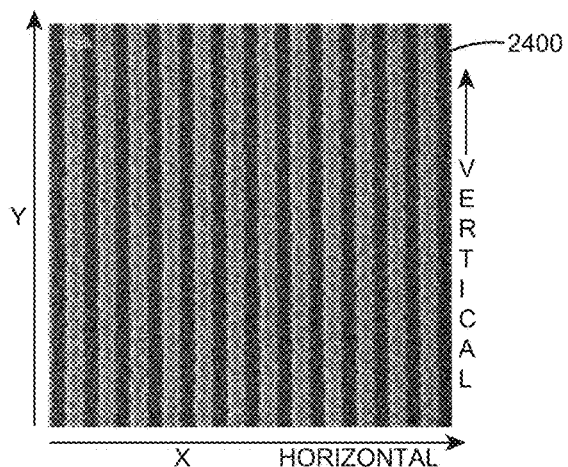
FIG. 24A is a grayscale representation of a pattern structure of vertical lines and spaces that the disclosed metrology tool analyzes.
Figure 24B:
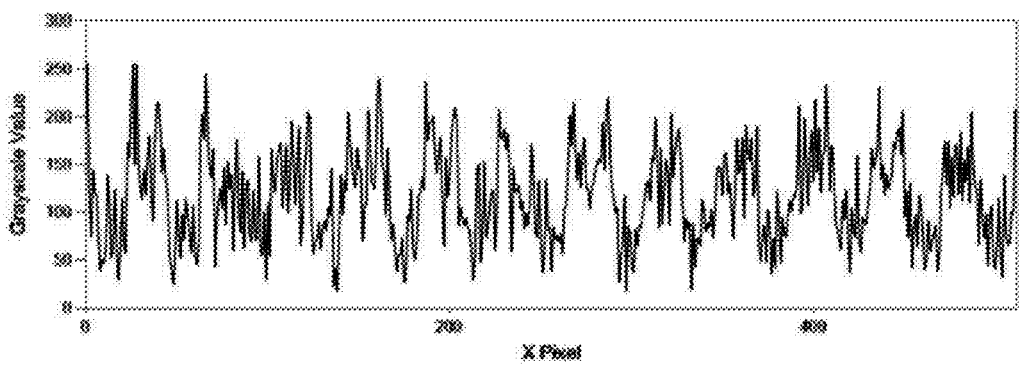
FIG. 24B shows a single linescan at one Y-pixel position.
Figure 24C:
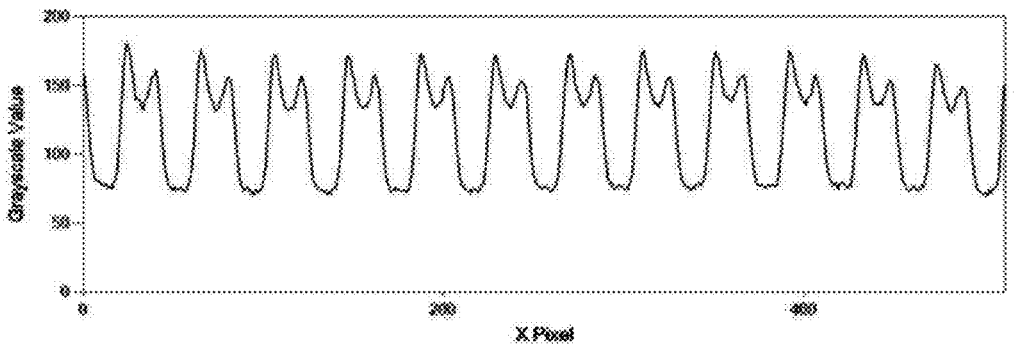
FIG. 24C shows the averaged linescan that is generated by averaging over all Y-pixels.

In the case of a pattern structure such as the vertical lines and spaces seen in the pattern structure 2400 of FIG. 24A, the inverse linescan metrology tool 765 averages vertically over the axis of symmetry to generate an average linescan, as per block 2320. An average linescan may be a grayscale value as a function of horizontal position wherein all of the vertical pixels have been averaged together. This averages out much of the SEM noise contained in the SEM image and produces a linescan that is more representative of the physical processes that generate a linescan without noise. FIG. 24B shows a single linescan at one Y-pixel position. FIG. 24C shows the averaged linescan that is generated by averaging over all Y-pixels.

While the example shown here is for vertical lines and spaces, any pattern with an axis of symmetry can be so processed to produce an average linescan. For example, long lines, long spaces, or long isolated edges can be so processed whenever the length of the line is sufficient to allow adequate averaging. Contact holes or pillars, with circular or elliptical symmetry, can also be averaged in a radial direction to produce an average linescan.

As per block 2325, tool 765 calibrates the inverse linescan model to the averaged linescan that was obtained in the manner described above. It is noted that the linescan model includes two kinds of parameters, namely 1) parameters that depend upon the materials and the properties of the SEM, and 2) parameters that depend on the geometry of the feature on the sample. Tool 765 can calibrate all of these parameters. Tool 765 finds the best fit of the model to the average linescan of FIG. 24C, as per block 2325. The values of the best fit parameters of the model are then the calibrated values.

That calibrated model is applied to a single linescan as shown in FIG. 24B. The best fit of the model to the single linescan of FIG. 24B is found, however, in this case tool 765 fixes all of the parameters that relate to the materials and SEM imaging tool. In this scenario, tool 765 varies only the parameters related to the geometry of the feature of the pattern structure in order to find the best fit of the calibrated model to a single linescan.

In a simplified scenario, the only parameters varied in block 2330 would be the positions of the edges of the feature. In one embodiment, it is assumed that the vertical dimension of the feature exhibits a predetermined thickness and that only the edge positions of the feature are varying. Next, the calibrated inverse linescan model is fit to every single horizontal cut through the 2D image of the feature, as per block 2330. We take the top horizontal row of pixels, and then the next row of pixels that are one pixel down, and then the next horizontal row of pixels down, and so forth. An example of one such single linescan is shown in FIG. 24B. The resulting best fit edge positions are the detected edges.

After the edges of the feature are detected in the manner described above, tool 765 may detect that the sample was rotated slightly during image acquisition, resulting in parallel tilted lines (that is, lines that are not perfectly vertical). Such tilting or rotation may contribute to inaccuracy of the detected edges by changing the average linescan and thus the calibrated ILM. Image rotation can be detected by fitting all the edges in the image to a set of parallel lines and determining their slope compared to vertical. If the slope is sufficiently different from the vertical case, the rotation should be removed. One possible criterion would be to compare the pixel position of the best fit line at the top of the image to the pixel position of the best fit line at the bottom of the image. If these pixel positions differ by some threshold, such as two pixels, then the image rotation is considered to be sufficiently large that its removal is required.

If such tilting/rotation is detected, as per block 2335, then the prior calibration is considered to be a first pass calibration and calibration is repeated. More particularly, if such tiling/rotation is detected, the rotation is subtracted out by shifting some rows of pixels to bring the edges into vertical alignment, as per block 2345, and calculating a new average linescan. Calibration of the model is then repeated as per block 2350 and 2325. Another fitting is performed as well, as per block 2330. Ultimately, tool 765 outputs geometry feature information (such as edge positions) describing the geometry of the feature that corresponds to the linescan image information provided to tool 765.

Like image rotation, the roughness of the features themselves contributes inaccuracies to the calibration of the ILM. Optionally, after a first pass edge detection, each row of pixels can be shifted to not only subtract out image rotation, but to subtract out the feature roughness as well. The final result after the shifting of each row of pixels is a vertical edge where the edge position varies by less than one pixel from a perfect vertical line. These shifted rows of pixels can then be averaged vertically to produce a more accurate average linescan for use in ILM calibration.

In actual practice, information handling system 760 may include an interface 757 coupled between processor 755 and an output device 770 such as a display, printer, or other device so that the user may observe the feature edges determined by metrology tool 765. Interface 757 may be a graphics interface, a printer interface, network interface, or other hardware interface appropriate for the particular type of output device 770.

While the embodiments described above make reference to the measurement of structures found on semiconductor wafers, as used in the manufacture of semiconductor devices, the invention is not limited to these applications. The invention can be usefully employed to measure the roughness of feature edges found on flat panel displays, microelectromechanical systems, microfluidic systems, optical waveguides, photonic devices, and other electronic, optical, or mechanical devices. Further, the invention can be used to measure the feature edge characteristics of naturally occurring structures such as crystals or minerals, or man-made structures such as nanoparticles or other nanostructures. Further, the invention can be used to measure the feature edge characteristics of biological samples as well.

While the embodiments described above make reference to measurements using a scanning electron microscope, the invention is not limited to that imaging tool. Other imaging tools, such as optical microscopes, stimulated emission and depletion (STED) microscopes, x-ray microscopes, transmission electron microscopes (TEM), focused ion beam microscopes, and helium ion microscopes, can also be used. Other forms of microscopes, such as scanning probe microscopes (atomic force microscopes (AFM) and scanning near-field optical microscopes (SNOM), for example) can be used as well.

While the embodiments described above make reference to top-down images of nominally planar pattern structures to measure edge roughness, the invention is not limited to such pattern structure geometries. Three-dimensional structures, non-flat structures, curved surfaces, or tilted structures can be measured using this invention. Besides edge roughness, surface roughness can be measured and analyzed using similar techniques as described in this invention.

While the embodiments described above make reference to the measurement of roughness, the invention can be used to make other measurements as well. For example, highly accurate determination of pattern structure edges can be used in the measurement of feature width, feature placement, edge placement, and other similar measures. Contours of measured features can be used for many purposes, such as modeling or controlling the performance of the measured device. By collecting and statistically averaging the measurement of many samples, even greater accuracy (lower uncertainty) can be obtained.

Consistent with the above disclosure, the examples of systems and methods enumerated in the following clauses are specifically contemplated and are intended as a non-limiting set of examples.

Clause 1. A method for determining roughness of a feature in a pattern structure, said method comprising:
generating, using an imaging device, a set of one or more images, each image of the set including one or more instances of a feature within a respective pattern structure, each image including measured linescan information corresponding to the pattern structure that includes noise;
detecting edges of the features within the pattern structure of each image of the set without filtering the images;
generating a biased power spectral density (PSD) dataset representing feature geometry information corresponding to the edge detection measurements of the set of images;
evaluating a high-frequency portion of the biased PSD dataset to determine a noise model for predicting noise over all frequencies of the biased PSD dataset; and
subtracting the noise predicted by the determined noise model from a biased roughness measure to obtain an unbiased roughness measure.

Clause 2. The method of clause 1, wherein said evaluating a high-frequency portion of the biased PSD dataset to determine a noise model comprises:

measuring a noise floor value in a high-frequency portion of the biased PSD dataset to determine a uniform value of predicted noise over all frequencies of the biased PSD dataset.

Clause 3. The method of any preceding clause, wherein said evaluating a high-frequency portion of the biased PSD dataset to determine a noise model comprises:
analyzing the biased PSD dataset to determine a set of noise model parameters defining a pink noise model having a non-uniform value of predicted noise over all frequencies of the biased PSD dataset.

Clause 4. The method of any preceding clause, wherein said analyzing the biased PSD dataset comprises:
measuring a noise floor value in a high-frequency portion of the biased PSD dataset;
subtracting the noise floor value from the biased PSD dataset to obtain an intermediate PSD dataset;
fitting a PSD roughness model to the intermediate PSD dataset;
determining a transition frequency at which the PSD roughness model decreases to less than a predetermined percentage of the measured noise floor value;
fitting the pink noise model to the biased PSD dataset over a range of frequencies greater than the transition frequency, to determine the set of noise model parameters for predicting noise over all frequencies of the biased PSD dataset.

Clause 5. The method of claim any preceding clause, wherein said analyzing the biased PSD dataset comprises:
fitting a combined model that accounts for both roughness and noise to the biased PSD dataset to obtain roughness parameters that represent an unbiased PSD dataset, and to determine the set of noise model parameters for predicting noise over all frequencies of the biased PSD dataset.

Clause 6. The method of claim any preceding clause, further comprising:
determining, before said fitting step, an initial estimate for each of the parameters in the combined roughness and noise model to use as starting values for the fitting step;
wherein said initial estimates are determined by:
measuring a noise floor value in a high-frequency portion of the biased PSD dataset;
subtracting the noise floor value from the biased PSD dataset to obtain an intermediate PSD dataset;
fitting a PSD roughness model to the intermediate PSD dataset;
determining a transition frequency at which the PSD roughness model decreases to less than a predetermined percentage of the measured noise floor value;
fitting a pink noise model to the biased PSD dataset over a range of frequencies greater than the transition frequency, to determine the set of noise model parameters for predicting noise over all frequencies of the biased PSD dataset;
subtracting the noise predicted by the pink noise model from the biased PSD dataset to obtain an unbiased PSD dataset; and
fitting a roughness model to the unbiased PSD dataset to obtain unbiased roughness parameters corresponding to the feature geometry information.

Clause 7. The method of claim any preceding clause, wherein the pink noise model is of the form:

$$PSD_{noise}(f) = \frac{PSD_{low} - PSD_{high}}{1 + |2\pi f \xi_{noise}|^B} + PSD_{high}$$

where $PSD_{low}$ represents the noise level in the low-frequency region, $PSD_{high}$ represents the noise level in the high-frequency region, $\xi_{noise}$ represents a correlation length of the noise, and B represents an exponential power that defines how fast the noise transitions from the low-frequency region to the high-frequency region.

Clause 8. The method of any preceding clause, wherein said detecting edges of the features within the pattern structure of each image of the set without filtering the images comprises:
measuring the pattern structure of each image of the set using an inverse linescan model (ILM) to detect the feature edges.

Clause 9. The method of any preceding clause, wherein said measuring the pattern structure comprises:
applying the measured linescan information to an inverse linescan model that relates measured linescan information to feature geometry information; and
determining, from the inverse linescan model, feature geometry information that describes feature edge positions of the predetermined feature of the pattern structure that corresponds to the measured linescan information.

Clause 10. The method of any preceding clause, wherein:
said biased roughness measure comprises the biased PSD dataset; and
said unbiased roughness measure comprises an unbiased PSD dataset.

Clause 11. The method of any preceding clause, further comprising:
analyzing the unbiased PSD dataset to obtain unbiased roughness parameters corresponding to the feature geometry information.

Clause 12. The method of any preceding clause, wherein analyzing the unbiased PSD dataset comprises:
fitting a roughness model to the unbiased PSD dataset to obtain the unbiased roughness parameters.

Clause 13. The method of any preceding clause, wherein said generating a biased PSD dataset comprises:
averaging individual PSD datasets from each measured feature of each image of the image set.

Clause 14. The method of any preceding clause, wherein the feature geometry information comprises at least one of feature width, or feature placement position.

Clause 15. A system for determining roughness of a feature in a pattern structure, said system comprising:
an imaging device for generating a set of one or more images, each image of the set including one or more instances of a feature within a respective pattern structure, each image including measured linescan information corresponding to the pattern structure that includes noise; and
a processor coupled to receive the measured linescan information from the imaging device, wherein said processor is configured to:
detect edges of the features within the pattern structure of each image of the set without filtering the images;
generate a biased power spectral density (PSD) dataset representing feature geometry information corresponding to the edge detection measurements of the set of images;
evaluate a high-frequency portion of the biased PSD dataset to determine a noise model for predicting noise over all frequencies of the biased PSD dataset; and subtract the noise predicted by the determined noise model from a biased roughness measure to obtain an unbiased roughness measure.

Clause 16. The system of clause 15, wherein, to evaluate a high-frequency portion of the biased PSD dataset to determine a noise model, the processor is further configured to:
measure a noise floor value in a high-frequency portion of the biased PSD dataset to determine a uniform value of predicted noise over all frequencies of the biased PSD dataset.

Clause 17. The system of any of clauses 15-16, wherein, to evaluate a high-frequency portion of the biased PSD dataset to determine a noise model, the processor is further configured to:
analyze the biased PSD dataset to determine a set of noise model parameters defining a pink noise model having a non-uniform value of predicted noise over all frequencies of the biased PSD dataset.

Clause 18. The system of any of clauses 15-17, wherein, to analyze the biased PSD dataset, the processor is further configured to:
measure a noise floor value in a high-frequency portion of the biased PSD dataset;
subtract the noise floor value from the biased PSD dataset to obtain an intermediate PSD dataset;
fit a PSD roughness model to the intermediate PSD dataset;
determine a transition frequency at which the PSD roughness model decreases to less than a predetermined percentage of the measured noise floor value;
fit the pink noise model to the biased PSD dataset over a range of frequencies greater than the transition frequency, to determine the set of noise model parameters for predicting noise over all frequencies of the biased PSD dataset.

Clause 19. The system of any of clauses 15-18, wherein, to analyze the biased PSD dataset, the processor is further configured to:
fit a combined model that accounts for both roughness and noise to the biased PSD dataset to obtain roughness parameters that represent an unbiased PSD dataset, and to determine the set of noise model parameters for predicting noise over all frequencies of the biased PSD dataset.

Clause 20. The system of any of clauses 15-19, wherein the processor is further configured to determine an initial estimate for each of the parameters in the combined roughness and noise model to use as starting values for fitting the combined model to the biased PSD dataset, wherein said initial estimates are determined by:
measuring a noise floor value in a high-frequency portion of the biased PSD dataset;
subtracting the noise floor value from the biased PSD dataset to obtain an intermediate PSD dataset;
fitting a PSD roughness model to the intermediate PSD dataset;
determining a transition frequency at which the PSD roughness model decreases to less than a predetermined percentage of the measured noise floor value;
fitting a pink noise model to the biased PSD dataset over a range of frequencies greater than the transition frequency, to determine the set of noise model parameters for predicting noise over all frequencies of the biased PSD dataset;
subtracting the noise predicted by the pink noise model from the biased PSD dataset to obtain an unbiased PSD dataset; and
fitting a roughness model to the unbiased PSD dataset to obtain unbiased roughness parameters corresponding to the feature geometry information.

Clause 21. The system of any of clauses 15-20, wherein the pink noise model is of the form:

$$PSD_{noise}(f) = \frac{PSD_{low} - PSD_{high}}{1 + |2\pi f \xi_{noise}|^B} + PSD_{high}$$

where $PSD_{low}$ represents the noise level in the low-frequency region, $PSD_{high}$ represents the noise level in the high-frequency region, $\xi_{noise}$ represents a correlation length of the noise, and B represents an exponential power that defines how fast the noise transitions from the low-frequency region to the high-frequency region.

Clause 22. The system of any of clauses 15-21, wherein, to detect edges of the features within the pattern structure of each image of the set without filtering the images, the processor is further configured to:
measure the pattern structure of each image of the set using an inverse linescan model (ILM) to detect the feature edges.

Clause 23. The system of any of clauses 15-22, wherein, to measure the pattern structure, the processor is further configured to:
apply the measured linescan information to an inverse linescan model that relates measured linescan information to feature geometry information; and
determine, from the inverse linescan model, feature geometry information that describes feature edge positions of the predetermined feature of the pattern structure that corresponds to the measured linescan information.

Clause 24. The system of any of clauses 15-23, wherein:
said biased roughness measure comprises the biased PSD dataset; and
said unbiased roughness measure comprises an unbiased PSD dataset.

Clause 25. The system of any of clauses 15-24, wherein the processor is further configured to analyze the unbiased PSD dataset to obtain unbiased roughness parameters corresponding to the feature geometry information.

Clause 26. The system of any of clauses 15-25, wherein, to analyze the unbiased PSD dataset, the processor is further configured to fit a roughness model to the unbiased PSD dataset to obtain the unbiased roughness parameters.

Clause 27. The system of any of clauses 15-26, wherein the processor is further configured to generate the biased PSD dataset by averaging individual PSD datasets from each measured feature of each image of the image set.

Clause 28. The system of any of clauses 15-28, wherein the feature geometry information comprises at least one of feature width, or feature placement position.

Clause 29. The method of any of clauses 1-14, wherein said detecting edges, generating a biased PSD, evaluating, and subtracting is performed by a processor coupled to the imaging device.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, no substantive distinction is intended between a PSD dataset and the PSD data included within such a dataset, unless the context clearly so requires.

Note that not all of the activities described above in the general description or the examples are required, that a portion of a specific activity may not be required, and that one or more further activities can be performed in addition to those described. Still further, the order in which activities are listed are not necessarily the order in which they are performed.

It can be advantageous to set forth definitions of certain words and phrases used throughout this patent document. The term "communicate," as well as derivatives thereof, encompasses both direct and indirect communication. The terms "include" and "comprise," as well as derivatives thereof, mean inclusion without limitation. The term "or" is inclusive, meaning and/or. The phrase "associated with," as well as derivatives thereof, can mean to include, be included within, interconnect with, contain, be contained within, connect to or with, couple to or with, be communicable with, cooperate with, interleave, juxtapose, be proximate to, be bound to or with, have, have a property of, have a relationship to or with, or the like. The phrase "at least one of," when used with a list of items, means that different combinations of one or more of the listed items can be used, and only one item in the list can be needed. For example, "at least one of: A, B, and C" includes any of the following combinations: A, B, C, A and B, A and C, B and C, and A and B and C.

The description in the present application should not be read as implying that any particular element, step, or function is an essential or critical element that must be included in the claim scope. The scope of patented subject matter is defined only by the allowed claims. Moreover, none of the claims invokes 35 U.S.C. § 112(f) with respect to any of the appended claims or claim elements unless the exact words "means for" or "step for" are explicitly used in the particular claim, followed by a participle phrase identifying a function. Use of terms such as (but not limited to) "mechanism," "module," "device," "unit," "component," "element," "member," "apparatus," "machine," "system," "processor," or "controller" within a claim is understood and intended to refer to structures known to those skilled in the relevant art, as further modified or enhanced by the features of the claims themselves, and is not intended to invoke 35 U.S.C. § 112(f).

Benefits, other advantages, and solutions to problems have been described above with regard to specific embodiments. However, the benefits, advantages, solutions to problems, and any feature(s) that can cause any benefit, advantage, or solution to occur or become more pronounced are not to be construed as a critical, required, or essential feature of any or all the claims.

After reading the specification, skilled artisans will appreciate that certain features are, for clarity, described herein in the context of separate embodiments, can also be provided in combination in a single embodiment. Conversely, various features that are, for brevity, described in the context of a single embodiment, can also be provided separately or in any subcombination. Further, references to values stated in ranges include each and every value within that range.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A method for determining roughness of a feature in a pattern structure, said method comprising:
    generating, using an imaging device, a set of one or more images, each image of the set including one or more instances of a feature within a respective pattern structure, each image including measured linescan information corresponding to the pattern structure that includes noise;
    detecting edges of the features within the pattern structure of each image of the set without filtering the images;
    generating a biased power spectral density (PSD) dataset representing feature geometry information corresponding to the edge detection measurements of the set of images;
    evaluating a high-frequency portion of the biased PSD dataset to determine a noise model for predicting noise over all frequencies of the biased PSD dataset; and
    subtracting the noise predicted by the determined noise model from a biased roughness measure to obtain an unbiased roughness measure.

2. The method of claim 1, wherein said evaluating a high-frequency portion of the biased PSD dataset to determine a noise model comprises:
    measuring a noise floor value in a high-frequency portion of the biased PSD dataset to determine a uniform value of predicted noise over all frequencies of the biased PSD dataset.

3. The method of claim 1, wherein said evaluating a high-frequency portion of the biased PSD dataset to determine a noise model comprises:
    analyzing the biased PSD dataset to determine a set of noise model parameters defining a pink noise model having a non-uniform value of predicted noise over all frequencies of the biased PSD dataset.

4. The method of claim 3, wherein said analyzing the biased PSD dataset comprises:
    measuring a noise floor value in a high-frequency portion of the biased PSD dataset;
    subtracting the noise floor value from the biased PSD dataset to obtain an intermediate PSD dataset;
    fitting a PSD roughness model to the intermediate PSD dataset;
    determining a transition frequency at which the PSD roughness model decreases to less than a predetermined percentage of the measured noise floor value;
    fitting the pink noise model to the biased PSD dataset over a range of frequencies greater than the transition frequency, to determine the set of noise model parameters for predicting noise over all frequencies of the biased PSD dataset.

5. The method of claim 3, wherein said analyzing the biased PSD dataset comprises:
fitting a combined model that accounts for both roughness and noise to the biased PSD dataset to obtain roughness parameters that represent an unbiased PSD dataset, and to determine the set of noise model parameters for predicting noise over all frequencies of the biased PSD dataset.

6. The method of claim 5, further comprising:
determining, before said fitting step, an initial estimate for each of the parameters in the combined roughness and noise model to use as starting values for the fitting step;
wherein said initial estimates are determined by:
measuring a noise floor value in a high-frequency portion of the biased PSD dataset;
subtracting the noise floor value from the biased PSD dataset to obtain an intermediate PSD dataset;
fitting a PSD roughness model to the intermediate PSD dataset;
determining a transition frequency at which the PSD roughness model decreases to less than a predetermined percentage of the measured noise floor value;
fitting a pink noise model to the biased PSD dataset over a range of frequencies greater than the transition frequency, to determine the set of noise model parameters for predicting noise over all frequencies of the biased PSD dataset;
subtracting the noise predicted by the pink noise model from the biased PSD dataset to obtain an unbiased PSD dataset; and
fitting a roughness model to the unbiased PSD dataset to obtain unbiased roughness parameters corresponding to the feature geometry information.

7. The method of claim 3, wherein the pink noise model is of the form:

$$PSD_{noise}(f) = \frac{PSD_{low} - PSD_{high}}{1 + |2\pi f \xi_{noise}|^B} + PSD_{high}$$

where $PSD_{low}$ represents the noise level in the low-frequency region, $PSD_{high}$ represents the noise level in the high-frequency region, $\xi_{noise}$ represents a correlation length of the noise, and B represents an exponential power that defines how fast the noise transitions from the low-frequency region to the high-frequency region.

8. The method of claim 1, wherein said detecting edges of the features within the pattern structure of each image of the set without filtering the images comprises:
measuring the pattern structure of each image of the set using an inverse linescan model (ILM) to detect the feature edges.

9. The method of claim 8, wherein said measuring the pattern structure comprises:
applying the measured linescan information to an inverse linescan model that relates measured linescan information to feature geometry information; and
determining, from the inverse linescan model, feature geometry information that describes feature edge positions of the predetermined feature of the pattern structure that corresponds to the measured linescan information.

10. The method of claim 1, wherein:
said biased roughness measure comprises the biased PSD dataset; and
said unbiased roughness measure comprises an unbiased PSD dataset.

11. The method of claim 10, further comprising:
analyzing the unbiased PSD dataset to obtain unbiased roughness parameters corresponding to the feature geometry information.

12. The method of claim 11, wherein analyzing the unbiased PSD dataset comprises:
fitting a roughness model to the unbiased PSD dataset to obtain the unbiased roughness parameters.

13. The method of claim 1, wherein said generating a biased PSD dataset comprises:
averaging individual PSD datasets from each measured feature of each image of the image set.

14. The method of claim 1, wherein the feature geometry information comprises at least one of feature width, or feature placement position.

15. A system for determining roughness of a feature in a pattern structure, said system comprising:
an imaging device for generating a set of one or more images, each image of the set including one or more instances of a feature within a respective pattern structure, each image including measured linescan information corresponding to the pattern structure that includes noise; and
a processor coupled to receive the measured linescan information from the imaging device, wherein said processor is configured to:
detect edges of the features within the pattern structure of each image of the set without filtering the images;
generate a biased power spectral density (PSD) dataset representing feature geometry information corresponding to the edge detection measurements of the set of images;
evaluate a high-frequency portion of the biased PSD dataset to determine a noise model for predicting noise over all frequencies of the biased PSD dataset; and
subtract the noise predicted by the determined noise model from a biased roughness measure to obtain an unbiased roughness measure.

16. The system of claim 15, wherein, to evaluate a high-frequency portion of the biased PSD dataset to determine a noise model, the processor is further configured to:
measure a noise floor value in a high-frequency portion of the biased PSD dataset to determine a uniform value of predicted noise over all frequencies of the biased PSD dataset.

17. The system of claim 15, wherein, to evaluate a high-frequency portion of the biased PSD dataset to determine a noise model, the processor is further configured to:
analyze the biased PSD dataset to determine a set of noise model parameters defining a pink noise model having a non-uniform value of predicted noise over all frequencies of the biased PSD dataset.

18. The system of claim 17, wherein, to analyze the biased PSD dataset, the processor is further configured to:
measure a noise floor value in a high-frequency portion of the biased PSD dataset;
subtract the noise floor value from the biased PSD dataset to obtain an intermediate PSD dataset;
fit a PSD roughness model to the intermediate PSD dataset;
determine a transition frequency at which the PSD roughness model decreases to less than a predetermined percentage of the measured noise floor value;

fit the pink noise model to the biased PSD dataset over a range of frequencies greater than the transition frequency, to determine the set of noise model parameters for predicting noise over all frequencies of the biased PSD dataset.

19. The system of claim 17, wherein, to analyze the biased PSD dataset, the processor is further configured to:

fit a combined model that accounts for both roughness and noise to the biased PSD dataset to obtain roughness parameters that represent an unbiased PSD dataset, and to determine the set of noise model parameters for predicting noise over all frequencies of the biased PSD dataset.

20. The system of claim 19, wherein the processor is further configured to determine an initial estimate for each of the parameters in the combined roughness and noise model to use as starting values for fitting the combined model to the biased PSD dataset, wherein said initial estimates are determined by:

measuring a noise floor value in a high-frequency portion of the biased PSD dataset;

subtracting the noise floor value from the biased PSD dataset to obtain an intermediate PSD dataset;

fitting a PSD roughness model to the intermediate PSD dataset;

determining a transition frequency at which the PSD roughness model decreases to less than a predetermined percentage of the measured noise floor value;

fitting a pink noise model to the biased PSD dataset over a range of frequencies greater than the transition frequency, to determine the set of noise model parameters for predicting noise over all frequencies of the biased PSD dataset;

subtracting the noise predicted by the pink noise model from the biased PSD dataset to obtain an unbiased PSD dataset; and fitting a roughness model to the unbiased PSD dataset to obtain unbiased roughness parameters corresponding to the feature geometry information.

21. The system of claim 17, wherein the pink noise model is of the form:

$$PSD_{noise}(f) = \frac{PSD_{low} - PSD_{high}}{1 + |2\pi f \xi_{noise}|^B} + PSD_{high}$$

where $PSD_{low}$ represents the noise level in the low-frequency region, $PSD_{high}$ represents the noise level in the high-frequency region, $\xi_{noise}$ represents a correlation length of the noise, and B represents an exponential power that defines how fast the noise transitions from the low-frequency region to the high-frequency region.

22. The system of claim 15, wherein, to detect edges of the features within the pattern structure of each image of the set without filtering the images, the processor is further configured to:

measure the pattern structure of each image of the set using an inverse linescan model (ILM) to detect the feature edges.

23. The system of claim 22, wherein, to measure the pattern structure, the processor is further configured to:

apply the measured linescan information to an inverse linescan model that relates measured linescan information to feature geometry information; and determine, from the inverse linescan model, feature geometry information that describes feature edge positions of the predetermined feature of the pattern structure that corresponds to the measured linescan information.

24. The system of claim 15, wherein:

said biased roughness measure comprises the biased PSD dataset; and said unbiased roughness measure comprises an unbiased PSD dataset.

25. The system of claim 24, wherein the processor is further configured to analyze the unbiased PSD dataset to obtain unbiased roughness parameters corresponding to the feature geometry information.

26. The system of claim 25, wherein, to analyze the unbiased PSD dataset, the processor is further configured to fit a roughness model to the unbiased PSD dataset to obtain the unbiased roughness parameters.

27. The system of claim 15, wherein the processor is further configured to generate the biased PSD dataset by averaging individual PSD datasets from each measured feature of each image of the image set.

28. The system of claim 15, wherein the feature geometry information comprises at least one of feature width, or feature placement position.

* * * * *